US008597661B2

(12) United States Patent
Kawaoka et al.

(10) Patent No.: US 8,597,661 B2
(45) Date of Patent: Dec. 3, 2013

(54) NEURAMINIDASE-DEFICIENT LIVE INFLUENZA VACCINES

(75) Inventors: Yoshihiro Kawaoka, Middleton, WI (US); Masato Hatta, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 884 days.

(21) Appl. No.: 12/113,690

(22) Filed: May 1, 2008

(65) Prior Publication Data

US 2009/0324640 A1 Dec. 31, 2009

Related U.S. Application Data

(60) Provisional application No. 60/927,638, filed on May 4, 2007.

(51) Int. Cl.
*A61K 39/145* (2006.01)

(52) U.S. Cl.
USPC .................. 424/209.1; 424/184.1; 424/204.1; 424/205.1; 424/206.1; 435/91.1

(58) Field of Classification Search
None
See application file for complete search history.

(56) References Cited

U.S. PATENT DOCUMENTS

| | | | | |
|---|---|---|---|---|
| 5,166,057 | A | 11/1992 | Palese et al. | |
| 5,786,199 | A | 7/1998 | Palese | |
| 5,854,037 | A | 12/1998 | Palese et al. | |
| 6,001,634 | A | 12/1999 | Palese et al. | |
| 6,271,011 | B1 | 8/2001 | Lee et al. | |
| 6,843,996 | B1 * | 1/2005 | Parkin et al. | 424/206.1 |
| 7,176,021 | B2 | 2/2007 | Kawaoka | |
| 7,226,774 | B2 | 6/2007 | Kawaoka | |
| 7,585,657 | B2 | 9/2009 | Kawaoka | |
| 2004/0002061 | A1 * | 1/2004 | Kawaoka | 435/5 |
| 2004/0132164 | A1 | 7/2004 | Doyle et al. | |
| 2004/0241139 | A1 | 12/2004 | Hobom et al. | |
| 2007/0141699 | A1 | 6/2007 | Kawaoka | |
| 2007/0231348 | A1 * | 10/2007 | Kawaoka et al. | 424/209.1 |
| 2008/0009031 | A1 | 1/2008 | Kawaoka | |
| 2009/0311669 | A1 | 12/2009 | Kawaoka | |

FOREIGN PATENT DOCUMENTS

| | | | |
|---|---|---|---|
| CA | 2379012 | | 1/2001 |
| EP | 1201760 | A1 | 5/2002 |
| JP | 07-203958 | | 8/1995 |
| WO | WO-00/60050 | A2 | 10/2000 |
| WO | WO-01/79273 | A2 | 10/2001 |
| WO | WO-03/068923 | A2 | 8/2003 |
| WO | WO-2006/051069 | A2 | 5/2006 |
| WO | WO-2008/147496 | A2 | 12/2008 |

OTHER PUBLICATIONS

"U.S. Appl. No. 11/509,249, Final Office Action mailed Jun. 6, 2008", 6 pgs.
"U.S. Appl. No. 11/509,249, Non Final Office Action with Restriction Requirement mailed Aug. 24, 2007", 9 pgs.
"U.S. Appl. No. 11/509,249, Notice of Allowance mailed Apr. 9, 2009", 7 pgs.
"U.S. Appl. No. 11/509,249, Notice of Allowance mailed Nov. 17, 2008", 4 pgs.
"U.S. Appl. No. 11/509,249, Response filed Feb. 20, 2008 to Non Final Office Action mailed Aug. 24, 2007", 11 pgs.
"U.S. Appl. No. 11/509,249, Response filed Oct. 6, 2008 to Office Action mailed Jun. 12, 2008", 11 pgs.
"U.S. Appl. No. 11/644,179 Final Office Action mailed Jul. 2, 2010", 8 pgs.
"U.S. Appl. No. 11/644,179, Non Final Office Action mailed Dec. 8, 2009", 7 pgs.
"U.S. Appl. No. 11/644,179, Response filed Jan. 30, 2008 to Restriction Requirement mailed Oct. 30, 2007", 5 pgs.
"U.S. Appl. No. 11/644,179, Response filed Apr. 8, 2010 to Non Final Office Action mailed Dec. 8, 2009", 8 pgs.
"Australian Application Serial No. 2003219745, Examiner's First Report mailed Feb. 14, 2007", 2 pgs.
"Australian Application Serial No. 2003219745, Response filed Mar. 14, 2008 to Examiner's First Report mailed Feb. 14, 2007", 24 pgs.
"Brazilian Application Serial No. PI 0307679-2, Office Action published in Patent Gazette No. 1871 of Nov. 14, 2006", 2 pgs.
"Brazilian Application Serial No. PI 0307679-2, Response filed Jan. 10, 2007 to Office Action mailed Nov. 14, 2006", 6 pgs.
"Canadian Application Serial No. 2,492,097, Office Action mailed Apr. 24, 2008", 3 pgs.
"Canadian Application Serial No. 2,492,097, Office Action mailed Jul. 31, 2009", 3 pgs.
"Canadian Application Serial No. 2,492,097, Response filed Jan. 29, 2010 to Office Action mailed Jul. 31, 2009", 13 pgs.
"Canadian Application Serial No. 2,492,097, Response filed Oct. 23, 2008 to Office Action mailed Apr. 24, 2008", 14 pgs.
"Chinese Application Serial No. 03808356.6, Office Action mailed Sep. 5, 2008", 6 pgs.
"Chinese Application Serial No. 03808356.6, Response filed Mar. 16, 2009 to Office Action mailed Sep. 5, 2008", 8 pgs.
"European Application Serial No. 02724994.5, Office Action mailed Mar. 27, 2009", 2 pgs.
"European Application Serial No. 03716017.3, Communication and Supplementary European Search Report mailed Jan. 2, 2008", 8 pgs.
"European Application Serial No. 03716017.3, Communication mailed May 23, 2006", 3 pgs.
"European Application Serial No. 03716017.3, Communication mailed Jul. 26, 2006", 2 pgs.
"European Application Serial No. 03716017.3, Communication mailed Oct. 20, 2008", 7 pgs.
"European Application Serial No. 03716017.3, Response filed Jul. 28, 2006 to Communication mailed May 23, 2006", 5 pgs.
"European Application Serial No. 03716017.3, Response filed Aug. 19, 2009 to Communication mailed Oct. 20, 2008", 17 pgs.
"International Application Serial No. PCT/US2003/004233, International Search Report mailed Dec. 16, 2005", 5 pgs.
"International Application Serial No. PCT/US2008/005641, Search Report mailed Feb. 4, 2009", 6 pgs.
"International Application Serial No. PCT/US2008/005641, Written Opinion mailed Feb. 4, 2009", 8 pgs.

(Continued)

*Primary Examiner* — Benjamin P Blumel
(74) *Attorney, Agent, or Firm* — Schwegman Lundberg & Woessner, P.A.

(57) ABSTRACT

Attenuated, neuraminidase deficient influenza virus, and compositions and methods to prepare that virus, are provided.

51 Claims, 8 Drawing Sheets

(56) References Cited

OTHER PUBLICATIONS

"Israel Application Serial No. 163,546, First Examination Report mailed Jul. 28, 2008", 2 pgs.
"Israel Application Serial No. 163,546, Office Action mailed Nov. 12, 2009", 2 pgs.
"Israel Application Serial No. 163,546, Response filed Nov. 27, 2008 to Office Action mailed Aug. 8, 2008", 13 pgs.
"Israel Application Serial No. 163,546, Substantive Examination Report mailed Feb. 23, 2009", 3 pgs.
"Israel Application Serial No. 163546, Office Action mailed Jun. 8, 2010".
"Japanese Application Serial No. 2003-315106, Notice of Allowance mailed Jan. 5, 2010", 5 pgs.
"Japanese Application Serial No. 2003-315106, Office Action mailed Jun. 24, 2009", 12 pgs.
"Japanese Application Serial No. 2003-315106, Response (Amended Claims, English translation) filed Oct. 15, 2009 to Office Action mailed Jun. 24, 2009", 9 pgs.
"Japanese Application Serial No. 2003-568038, Amendment filed Aug. 19, 2005", 13 pgs.
"Japanese Application Serial No. 2003-568038, Notice of Allowance mailed Nov. 30, 2009", 5 pgs.
"Japanese Application Serial No. 2003-568038, Office Action mailed May 15, 2009", 7 pgs.
"Japanese Application Serial No. 2003-568038, Office Action mailed Jul. 10, 2008", 6 pgs.
"Japanese Application Serial No. 2003-568038, Office Action mailed Jul. 21, 2005", 6 pgs.
"Japanese Application Serial No. 2003-568038, Response filed Dec. 10, 2008 to Office Action mailed 06-19-7-10-08", 18 pgs.
"Korean Application Serial No. 10-2004-7012647, Office Action mailed Feb. 26, 2010", (w/ English Translation), 7 pgs.
"Mexican Application Serial No. PA/a/2004/007914, Notice of Allowance mailed Jul. 30, 2008", 2pgs.
"Mexican Application Serial No. PA/a/2004/007914, Office Action mailed Feb. 14, 2008", 3 pgs.
"Mexican Application Serial No. PA/a/2004/007914, Office Action mailed Feb. 22, 2008", 4 pgs.
"Mexican Application Serial No. PA/a/2004/007914, Response filed Jun. 11, 2008 to Office Action mailed Feb. 22, 2008", 70 pgs.
"Nucleotide sequences of influenza virus segments 1 and 3 reveal mosaic structure of a small viral RNA segment", *Database Uniprot*, (Nov. 14, 2001), 2 pgs.
Bilsel, P., et al., "Mutations in the Cytoplasmic Tail of Influenza A Virus Neuraminidase Affect Incorporation into Virions", *Journal of Virology*, 67(11), (Nov. 1993), 6762-6767.
Brandli, A. W, et al., "A Polarized Epithelial Cell Mutant Deficient in Translocation of UDP-galactose into the Golgi Complex", *Journal of Biological Chemistry*, 263(31), (Nov. 5, 1988), 16283-16290.
Castrucci, M. R, et al., "Attenuation of Influenza a Virus by Insertion of a Foreign Epitope into the Neuraminidase", *Journal of Virology*, 66(8), (1992), 4647-4653.
Castrucci, M. R, et al., "Protection against Lethal Lymphocytic Choriomeningitis Virus (LCMV) Infection by Immunization of Mice with an Influenza Virus Containing an LCMV Epitope Recognized by Cytotoxic T Lymphocytes", *Journal of Virology*, vol. 68(6), (Jun. 1994), 3486-3490.
Castrucci, M. R., et al., "Biologic Importance of Neuraminidase Stalk Length in Influenza A Virus", *Journal of Virology*, 67(2), (1993), 759-764.
Crescenzo-Chaigne, B., et al., "Comparative analysis of the ability of the polymerase complexes of influenza viruses type A, B and C to assemble into functional RNPs that allow expression and replication of heterotypic model RNA templates in vivo", *Virology*, 265(2), (Dec. 1999), 342-353.
Desselberger, U., et al., "The 3' and 5'-terminal sequences of influenza A, B and C virus RNA segments are highly conserved and show partial inverted complementarity", *Gene*, 8 (3), (Feb. 1980), 315-328.
Dollenmaier, G., et al., "Membrane-Associated Respiratory Syncytial Virus F Protein Expressed From A Human Rhinovirus Type 14 Vector Is Immunogenic", *Virology*, 281(2), (Mar. 15, 2001), 216-230.
Duhaut, S., et al., "Approximately 150 Nucleotides from the 5' End of an Influenza a segment 1 Defective Virion RNA Are needed for Genome Stability during passage of Defective Virus in Infected Cells", *Virology*, 275(2), (2000), 278-285.
Duhaut, S., et al., "Approximately 150 nucleotides from the 5' end of an influenza A segment 1 defective virion RNA are needed for genome stability during passage of defective virus in infected cells.", *Virology*, 275(2), (Sep. 30, 2000), 278-285.
Duhaut, S. D, et al., "Heterologous Protection of Misce from a lethal human HINI Influenza A Virus Infection by H3NB Equine Defective Interfering Virus: Comparison of Defective RNA Sequences Isolated from the DI Inoculum and Mouse Lung", *Virology*, 248(2), (1998), 241-253.
Durbin, A. P, et al., "Human Parainfluenza Virus Type 3 (PIV3) Expressing The Hemagglutinin Protein Of Measles Virus Provides A Potential Method For Immunization Against Measles Virus and PIV3 In Early Infancy", *Journal of Virology*, 74(15), (Aug. 2000), 6821-6831.
Fujii, Y, et al., "The packaging of influenza viral genome", *Virus*, 52(1), Uirusu (Japanese Journal Name), (Jun. 2002), 203-206.
Garcia-Sastre, A., et al., "Introduction of Foreign Sequences into the Genome of Influenza A Virus", *Dev. Biol. Stand.* vol. 82, (1994), 237-246.
Garcia-Sastre, A., et al., "Use of a Mammalian Internal Ribosomal Entry Site Element for Expression of a Foreign Protein by a Transfectant Influenza Virus", *Journal of Virology*, 68(10), (Oct. 1994), 6254-6261.
Ghate, A. A, et al., "Influenza Type B Neuraminidase Can Replace the Function of Type A Neuraminidase", *Virology*, 264 (2), (Nov. 1999), 265-277.
Gilleland, H. E, et al., "Chimeric Influenza Virus Incorporating Epitopes of Outer Membrane Protein F as a Vaccine Against Pulmonary Infection with *Pseudomonas Aeruginosa", Behring Inst. Mitt. 98*, (Feb. 1997), 291-301.
Hiti, A. L., et al., "P03470—Neuraminidase", Entrez Protein Database, http://www.ncbi.nlm.nih.gov/entrez/viewer.fcgi?db=protein&val=84028231, (1982), 730-734.
Hughes, Mark T, "Adaptation of Influenza A Viruses to Cells Expressing Low Levels of Sialic Acid Leads to Loss of Neuraminidase Activity", *Journal of Virology*, 75 (8), (Apr. 2001), 3766-3770.
Hughes, Mark T, "Influenza A Viruses Lacking Sialidase Activity Can Undergo Multiple Cycles of Replication in Cell Culture, Eggs, or Mice", *Journal of Virology*, 74 (11), (Jun. 2000), 5206-5212.
Ito, T, et al., "Differences in Sialic Acid-Galactose Linkages in the Chicken Egg Amnion and Allantois Influence Human Influenza Virus Receptor Specificity and Variant Selection", *Journal of Virology*, 71 (4), (Apr. 1997), 3357-3362.
Jin, H., et al., "Imparting temperature sensitivity and attenuation in ferrets to A/Puerto Rico/8/34 influenza virus by transferring the genetic signature for temperature sensitivity from cold-adaptive A/Ann Arbor/ 6/60", *Journal of Virology*, 78(2), (Jan. 2004), 995-998.
Li, S, et al., "Recombinant influenza A virus vaccines for the pathogenic human A/Hong/Kong/97 (H5N1) Viruses", *Journal of Infectious Diseases*,179(5), (1999), 1132-1138.
Li, S., et al., "Influenza A Virus Transfectants with Chimeric Hemagglutinins containing Epitopes from different subtypes", *Journal of Virology* 66(1), (1992), 399-404.
Liu, Chongguang, "Influenza type A virus neuraminidase does not play a role in viral entry, replication, assembly, or budding.", *Journal of Virology*, 69(2), (Feb. 1995), 1099-106.
Liu, Chongguang, "Selection and characterization of a neuraminidase-minus mutant of influenza virus and its rescue by cloned neuraminidase genes.", *Virology*, 194(1), (1993), 403-407.
Luytjes, W., "Amplification, Expression, and Packaging of a Foreign Gene by Influenza Virus", *Cell*, 59(6), (1989), 1107-1113.

(56) References Cited

OTHER PUBLICATIONS

Martin, J., et al., "Studies of the Binding Properties of Influenza Hemagglutinin Receptor-Site Mutants", *Virology*, 241(1), (Feb. 1, 1998), 101-111.
Masuda, H., et al., "Substitution of Amino Acid Residue in Influenza A Virus Hemagglutinin Affects Recognition of Sialyl-Oligosaccharides Containing N-Glycolylneuraminic Acid", FEBS Letters, 464, (1999), 71-74.
Matta, M, et al., "Cell-Surface Sialoglycoconjugate Structures in Wild-Type and Mutant *Crithidia fasciculata", Parasitol Res*, 85, (1999), 293-299.
Mishin, V. P, et al., "Protection afforded by intranasal immunization with the neuraminidase-lacking mutant of influenza A virus in ferret model", *Vaccine*,23(22), (2005), 2922-2927.
Mitnaul, Lyndon J, et al., "Balanced Hemagglutinin and Neuraminidase Activities are Critical for Efficient Replication of Influenza A Virus", *Journal of Virology*, 74 (13), (Jul. 2000), 6015-6020.
Murphy, B. R, et al., "An Influenza A live attenuated reassortant virus possessing three temperature-sensitive mutations in the PB2 Polymerase gene rapidly loses temperature sensitivity following replication in hamsters", *Vaccine*, 15 (12-13), (1997), 1372-1378.
Muster, T., "An Influenza A Virus Containing Influenza B Virus 5' and 3' Noncoding Regions on the Neuraminidase Gene is Attenuated in Mice", *Proceeding of the National Academy of Sciences USA*, 88, (Jun. 1991), 5177-5181.
Neumann, Gabriele, et al., "Generation of Influenza A Viruses Entirely from Cloned cDNAs", *Proceedings of the National Academy of Sciences USA*, 96, (Aug. 1999), 9345-9350.
Neumann, Gabriele, et al., "Influenza A virus NS2 protein mediates vRNP nuclear export through NES-independent interaction with hCRM1", *The EMBO Journal*, 19 (24), (2000), 6751-6758.
Neumann, Gabriele, et al., "Mutational Analysis of Influenza Virus Promoter Elements In Vivo", *Journal of General Virology* (1995), 76, (Feb. 24, 1995), 1709-1717.
Percy, N., et al., "Expression of a foreign protein by influenza A virus.", *J. Virol., 68*(7), (Jul. 1994), 4486-4492.
Piatti, G., "Identification of Immunodominant Epitopes In The Filamentous Hemagglutinin of *Bordetella pertusis", FEMS Immunology and Medical Microbiology*, 23(3), (Mar. 1999), 235-241.
Portela, A., et al., "Replication of orthomyxoviruses", *Advances in Virus Research*, 54, (1999), 319-348.
Ray, Manas K, et al., "A novel glycosylation phenotype expressed by Lec23, a Chinese hamster ovary mutant deficient in α-glucosidase I", *Journal of Biological Chemistry*, 266(34), (Dec. 5, 1991), 22818-22825.
Restifo, N. P, et al., "Transfectant influenza A viruses are effective recombinant immunogens in the treatment of experimental cancer.", *Virology*, 249(1), (Sep. 15, 1998), 89-97.
Rodrigues, M., et al., "Influenza and vaccinia viruses expressing *malaria* $CD8^+$ T and B cell epitopes. Comparison of their immunogenicity and capacity to induce protective immunity", *J Immunol.*, 153(10), (Nov. 15, 1994), 4636-48.
Schultz-Cherry, S., et al., "Influenza Virus NS1 Protein Induces Apoptosis in Cultured Cells", *Journal of Virology*, 75, (Sep. 2001), 7875-7881.
Shinya, K., et al., "Characterization of a neuraminidase-deficient influenza a virus as a potential gene delivery vector and a live vaccine", *Journal of Virology*, 78(6), (Mar. 2004), 3083-3088.
Strobel, I., et al., "Efficient Expression Of The Tumor-Associated Antigen MAGE-3 In Human Dendritic Cells, Using An Avian Influenza Virus Vector", *Human Gene Therapy*, 11(16), (Nov. 1, 2000), 2207-2218.
Takeda, T., et al., "Expression of Podocalyxin Inhibits Cell-Cell Adhesion and Modifies Junctional Properties in Madin-Darby Canine Kidney Cells", *Molecular Biology of the Cell*, 11, (Sep. 2000), 3219-3232.
Walker, W. S, et al., "HEL-Flu: an influenza virus containing the hen egg lysozyme epitope recognized by $CD4^+$ T cells from mice transgenic for an αβTCR", *J. Immunol.*, 159(6), (Sep. 1997), 2563-2566.
Yang, Ping, "Hemagglutinin specificity and neuraminidase coding capacity of neuraminidase-deficient influenza viruses.", *Virology*, 229(1), (1997), 155-165.
"U.S. Appl. No. 11/644,179, Response filed Aug. 17, 2010 to Final Office Action mailed Jul. 2, 2010", 8 pgs.
"Australian Application Serial No. 2008203186, Office Action Received mailed Sep. 16, 2010", 1 page.
"European Application Serial No. 03716017.3, Office Action mailed Jul. 27, 2010", 4 pgs.
"Israel Application Serial No. 163546, Office Action Response Filed Oct. 20, 2010", 10 pgs.
"Korean Application Serial No. 10-2004-7012647, Amendment and Response filed Jun. 10, 2010 to Office Action mailed Feb. 26, 2010", 17 pgs.
"Korean Application Serial No. 10-2010-7011520, Office Action mailed Aug. 4, 2010", (English Translation), 2 pgs.
"Korean Application Serial No. 10-2010-7011520, Office Action Response Filed Oct. 20, 2010", 30 pgs.
Garcia-Sastre, A., et al., "Introduction of foreign sequences into the genome of influenza A virus.", Dev Biol Stand., 82, (1994), 237-46.
Stray, Stephen J., et al., "Influenza Virus Infection of Desialylated Cells", Glycobiology, vol. 10, No. 7, (2000), 649-658.
"U.S. Appl. No. 12/470,287, Response filed Apr. 28, 2011 to Restriction Requirement mailed Dec. 29, 2010", 8 pgs.
"U.S. Appl. No. 12/470,287, Restriction Requirement mailed Dec. 29, 2010", 6 pgs.
"Australian Application Serial No. 2008203186, First Examiner Report mailed Jan. 28, 2011", 2 pgs.
"Australian Application Serial No.2008203186, Subsequent Examiner Report mailed Apr. 13, 2011", 2 Pgs.
"Canadian Application Serial No. 11/509,249, Response filed May 16, 2011 to Office Acttion mailed Nov. 18, 2010", 15 pgs.
"Canadian Application Serial No. 2492097, Office Action mailed Nov. 18, 2010", 4 pgs.
"European Application Serial No. 03716017.3, Response filed Feb. 4, 2011 to Office Action mailed Jul. 27, 2010", 12 pgs.
"Korean Application Serial No. 10-2010-7011520, Amended Claims filed May 24, 2011 in Response to Office Action mailed Mar. 10, 2011", (English Translation of Amended Claims), 4 pgs.
"Korean Application Serial No. 10-2010-7011520, Office Action mailed Feb. 24, 2011", (w/ English Translation), 5 pgs.

* cited by examiner

VN1194NA- AND NAeGFP VIRUSES (PASSAGE 10) IN MDCK CELLS

VN1194NA-

VN1194NAeGFP

VN1194NAeGFP IN HNE CELLS
(HUMAN NASAL EPITHELIAL CELLS)

VIRULENCE AND TISSUE TROPISM OF VN1194NA-VIRUS

| Virus | $MLD_{50}$ (PFU)[a] | Tissue tropism[b] | | | | | | | | | |
|---|---|---|---|---|---|---|---|---|---|---|---|
| | | Days after infection | Virus titer (mean $log_{10}$ PFU ± SD/g) in: | | | | | | | | |
| | | | Lungs | Nasal turbinates | Spleen | Heart | Kidneys | Brain | Pancreas | Colon | Liver |
| VN1194 | 3.1 | 3 | 6.7±0.2 | 4.8±0.9 | 5.6±0.1 | 4.6±0.7 | 3.3±0.6 | 1.5±0.1 | - | 3.7±0.5 | 1.7±0.1 |
| | | 6 | 7.7±0.7 | 6.9±0.9 | 3.6±0.9 | 7.3±0.8 | 6.2±0.3 | 6.3±0.8 | 3.9±1.2 | 4.2, 5.4 | 3.5±1.5 |
| VN1194NA- | >$10^5$ | 3 | - | 3.4<br>3.6 | - | - | - | - | - | - | - |
| | | 6 | - | 1.7<br>2.2 | - | - | - | - | - | - | - |

*FIG. 5*

VIRUS TITERS IN CHALLENGED MICE ON DAY 3 POST-CHALLENGE

| Challenge virus | Group | Tissue tropism: Virus titer (mean $\log_{10}$ PFU ± SD/g) in: Lungs | Nasal turbinates | Spleen | Kidneys | Brain |
|---|---|---|---|---|---|---|
| VN1194 | Vaccine | 3.1, 5.1, 5.2, 5.4, 5.7 | 1.7 | - | - | - |
| | Control | 6.6±0.1 | 5.1±1.1 | 4.5±1.1 | 1.9, 2.4, 2.9, 6.0 | 1.4, 1.4, 1.4, 2.1 |
| VN1203 | Vaccine | 6.2±0.4 | 2.8 | - | - | - |
| | Control | 7.4±0.1 | 1.9, 4.1 | 4.5±0.3 | 1.5, 1.5, 1.7, 2.0, 4.0 | - |
| Indonesia7 | Vaccine | 6.9±0.8 | 1.9, 4.2 | - | - | - |
| | Control | 8.8±0.1 | 5.8±0.9 | 4.8±0.3 | 3.6±0.9 | 1.3, 1.4, 1.7, 1.9 |

*FIG. 8*

VIRUS TITERS IN CHALLENGED MICE ON DAY 6 POST-CHALLENGE

| Challenge virus | Group | Tissue tropism: Virus titer (mean $\log_{10}$ PFU ± SD/g) in: Lungs | Nasal turbinates | Spleen | Kidneys | Brain |
|---|---|---|---|---|---|---|
| VN1194 | Vaccine | 2.6 | - | - | - | - |
| | Control | 7.3±0.3 | 6.7±0.6 | 3.3±0.4 | 5.9±0.3 | 5.6±0.2 |
| VN1203 | Vaccine | 1.7, 2.8, 4.1, 5.0, 5.6 | - | - | - | - |
| | Control | 6.5±0.3 | 4.5±1.1 | 2.8±0.2 | 3.7, 3.8, 3.8, 4.1, 4.2 | 4.1±0.8 |
| Indonesia7 | Vaccine | 4.4, 4.5, 5.1 | - | - | - | - |
| | Control | 6.9±0.1 | 5.6±0.5 | 3.0±0.1 | 2.2, 3.7, 4.6, 5.0, 5.2 | 3.8±1.2 |

*FIG. 9*

NEURAMINIDASE-DEFICIENT LIVE INFLUENZA VACCINES

CROSS-REFERENCE TO RELATED APPLICATIONS

This application claims the benefit of the filing date of U.S. application Ser. No. 60/927,638, filed May 4, 2007, the disclosure of which is incorporated by reference herein.

STATEMENT OF GOVERNMENT RIGHTS

The invention was made at least in part with a grant from the Government of the United States of America (grant AI044386 from the National Institutes of Health). The Government has certain rights to the invention.

BACKGROUND

The family Orthomyxoviridae comprises influenza A, B, and C viruses, and Thogoto- and isavirus (Cox et al., 2005; Lamb et al., 2001). Influenza pandemics in humans are caused by influenza A viruses. Influenza A viruses contain 8 single-stranded, negative-sense viral RNAs (vRNAs) that encode 10-11 proteins (Cox et al., 2005; Lamb et al., 2001). The viral replication complex comprises three polymerase proteins (PB2, PB1, and PA), encoded by the three largest genome segments, and the nucleoprotein (NP), which is encoded by segment 5. The M1 viral matrix protein and the M2 ion channel protein are both encoded by segment 7 and translated from unspliced or spliced mRNAs, respectively. Two proteins are also encoded by segment 8: NS1, derived from an unspliced RNA, counteracts the cellular interferon response and NEP, derived from a spliced RNA, is a nuclear export protein. NEP mediates the transport to the cytoplasm of newly synthesized viral ribonucleoprotein complexes (vRNPs, composed of viral RNA and the polymerase and NP proteins).

Influenza A viruses contain two surface glycoproteins, hemagglutinin (HA) and neuraminidase (NA), that are encoded by segments 4 and 6, respectively (Cox et al., 2005; Lamb et al., 2001; Wiley et al., 1997). The HA protein is the major viral antigen and mediates virus binding to sialic acid-containing receptors on the cell surface. It is synthesized as a single polypeptide and subsequently cleaved into HA1 and HA2 subunits. HA cleavage is required for infectivity (Garten et al., 1999), because it generates the hydrophobic N-terminus of HA2, which mediates fusion between the viral envelope and the cell membrane. The NA protein cleaves α-ketosidic linkages between a terminal sialic acid and the adjacent sugar residue. The removal of sialic acids from cell surface sialyloligosaccharides, as well as from the HA and NA proteins, facilitates virus release from the cell surface and prevents virus self-aggregation. For optimal virus replication, the receptor-binding activity of HA and the receptor-destroying activity of NA are balanced (Wagner et al., 2002).

Localized, annual outbreaks of influenza, also called 'seasonal influenza', are caused by 'antigenic drift', where point mutations in the HA (or HA and NA) proteins allow virus variants to evade the human immune response. During epidemics, infection rates of 10%-20% are typical but can reach 50% in small groups. An estimated 20,000-40,000 people die from influenza-related illness annually in the U.S., creating a substantial economic burden, estimated at $17.5 billion in 1998 in direct costs (i.e., medications, hospitalizations, and physicians visits) and an additional $5.4 billion in indirect costs (i.e., loss of productivity).

Influenza pandemics are caused by 'antigenic shift', that is, the introduction of new HA (or new HA and NA) subtypes into the human population. The lack of prior exposure to the new HA (or new HA and NA) subtypes creates a population that is immunologically naïve to the antigenic shift variants, resulting in extremely high infection rates and rapid, worldwide virus spread. During the last century, three influenza pandemics have occurred. In 1957 and 1968, the 'Asian influenza' and 'Hong Kong influenza' killed an estimated 70,000 and 33,800 people in the U.S., respectively. Both pandemic viruses arose from reassortment of human and avian strains. In 1957, H2 HA and N2 NA genes of avian origin were introduced into a human virus. In 1968, the H2 HA gene was replaced with an avian H3 HA gene. The 1918/1919 'Spanish influenza' is the most devastating infectious disease on record. An estimated 20-50 million people died worldwide and life expectancy in the U.S. was reduced by 10 years. The causative agent of 'Spanish influenza' was an H1N1 influenza A virus, which may have been introduced into human populations from an avian species. Estimates for future pandemics range from about 300,000 to 10 million hospitalizations in the U.S. and from about 90,000 excess deaths in the U.S. to up to 360 million excess deaths worldwide. The human toll and economic burden of future influenza pandemics would thus be extraordinary.

Although highly pathogenic H5N1 viruses have not (yet) caused a human pandemic, their continued transmission to humans and high mortality rate in humans have made the development of vaccines to these viruses a priority. The first transmission of highly pathogenic H5N1 avian influenza viruses to humans occurred in Hong Kong in 1997, when 6 of the 18 individuals infected succumbed to the infection. Since 2003, highly pathogenic H5N1 avian influenza viruses have become prevalent in Southeast Asia and endemic in poultry in some countries in this region. By the spring of 2006, these viruses had also spread to Europe and Africa.

Currently, two general types of influenza vaccines are available: inactivated and live vaccines. Inactivated vaccines are safe, but they induce humoral, not cellular, immune responses. Thus, the efficacy of inactivated vaccines is limited. On the other hand, live vaccines are more efficacious than inactivated vaccines since they induce both humoral and cellular immune responses. However, the safety of live vaccines varies.

Thus, there is a need for improved influenza vaccines.

SUMMARY OF THE INVENTION

To overcome the limitations of current vaccines, the present invention provides compositions and methods to prepare live, attenuated virus stocks for use in live vaccines, as well as live vaccines. In particular, the present invention provides for a live, attenuated influenza vaccine based on an isolated influenza virus lacking a NA gene segment. As described herein, the $NA^-$ influenza virus was generated by reverse genetics and, after several passages, the virus grew to titers suitable for use as a vaccine. Because this virus lacks functional sialidase activity, it is attenuated (avirulent) and innocuous. However, as described herein, the $NA^-$ influenza virus can infect animals and induce humoral as well as cellular immune responses. Thus, the 7 segment influenza virus vaccine is safe, but highly efficacious. Moreover, the $NA^-$ virus can be used as a gene therapy vector, where one or more genes of interest are introduced to one of the 7 influenza virus gene segments, or on one or more additional influenza virus gene segments.

Thus, the invention provides a composition to prepare a 7 segment influenza A or B virus. The composition includes one or more vectors which include transcription cassettes for vRNA production and transcription cassettes for mRNA production. The transcription cassettes for vRNA production include a transcription cassette having a promoter operably linked to an influenza virus PA cDNA linked to a transcription termination sequence, a transcription cassette having a promoter operably linked to an influenza virus PB1 cDNA linked to a transcription termination sequence, a transcription cassette having a promoter operably linked to an influenza virus PB2 cDNA linked to a transcription termination sequence, a transcription cassette having a promoter operably linked to an influenza virus HA cDNA linked to a transcription termination sequence, a transcription cassette having a promoter operably linked to an influenza virus NP cDNA linked to a transcription termination sequence, a transcription cassette having a promoter operably linked to an influenza virus M cDNA linked to a transcription termination sequence, and a transcription cassette having a promoter operably linked to an influenza virus NS cDNA linked to a transcription termination sequence. The transcription cassettes for mRNA production include a transcription cassette having a promoter operably linked to a DNA coding region for influenza virus PA linked to a transcription termination sequence, a transcription cassette having a promoter operably linked to a DNA coding region for influenza virus PB1 linked to a transcription termination sequence, a transcription cassette having a promoter operably linked to a DNA coding region for influenza virus PB2 linked to a transcription termination sequence, and a transcription cassette having a promoter operably linked to a DNA coding region for influenza virus NP linked to a transcription termination sequence. The composition thus includes 7 transcription cassettes for vRNA production and 4 or more transcription cassettes for mRNA production. The composition does not include sequences corresponding to NA coding or noncoding sequences for vRNA production, or does not include sequences corresponding to NA coding or noncoding sequences for vRNA production and sequences for mRNA production of NA.

The promoter or transcription termination sequence in a transcription cassette for vRNA or virus protein expression (mRNA production) may be the same or different relative to the promoter or transcription termination sequence in any other cassette. Preferably, the cassette which expresses influenza vRNA comprises a promoter suitable for expression in at least one particular host cell, e.g., avian or mammalian host cells such as canine, feline, equine, bovine, ovine, or primate cells including human cells, or preferably, for expression in more than one host.

In one embodiment, one or more transcription cassettes for vRNA production have a promoter including, but not limited to, a RNA polymerase I promoter, e.g., a human RNA polymerase I promoter, a RNA polymerase II promoter, a RNA polymerase III promoter, a T7 promoter, or a T3 promoter. Preferred transcription termination sequences for the vRNA vectors include, but are not limited to, a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes. Each promoter or transcription termination sequence in each transcription cassette may be the same or different than the promoters or transcription termination sequences in other cassettes. For instance, each RNA polymerase I promoter or transcription termination sequence in each transcription cassette may be the same or different as the RNA polymerase I promoter or transcription termination sequence in any other transcription cassette, each RNA polymerase II promoter or transcription termination sequence in each transcription cassette may be the same or different as the RNA polymerase II promoter or transcription termination sequence in any other transcription cassette, and each ribozyme sequence in each transcription cassette may be the same or different as the ribozyme sequences in any other cassette. In one embodiment, one or more transcription cassettes for vRNA comprise a RNA polymerase II promoter linked to a ribozyme sequence linked to viral coding sequences linked to another ribozyme sequences, optionally linked to a RNA polymerase II transcription termination sequence. In one embodiment, the ribozyme sequences in a single cassette are not the same. In one embodiment, at least 2 and preferably more, e.g., 3, 4, 5, 6, or 7, transcription cassettes for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence.

A plurality of the transcription cassettes of the invention may be physically linked or each transcription cassette may be present on an individual vector such as a plasmid or other, e.g., linear, nucleic acid delivery vehicle.

Also provided is a composition to prepare a 7 segment influenza A or B virus. The composition includes one or more vectors which include transcription cassettes for vRNA production. The transcription cassettes include a transcription cassette having a promoter operably linked to an influenza virus PA cDNA linked to a transcription termination sequence, a transcription cassette having a promoter operably linked to an influenza virus PB1 cDNA linked to a transcription termination sequence, a transcription cassette having a promoter operably linked to an influenza virus PB2 cDNA linked to a transcription termination sequence, a transcription cassette having a promoter operably linked to an influenza virus HA cDNA linked to a transcription termination sequence, a transcription cassette having a promoter operably linked to an influenza virus NP cDNA linked to a transcription termination sequence, a transcription cassette having a promoter operably linked to an influenza virus M cDNA linked to a transcription termination sequence, and a transcription cassette having a promoter operably linked to an influenza virus NS cDNA linked to a transcription termination sequence. The composition does not include sequences corresponding to NA coding or noncoding sequences for vRNA production, or does not include sequences corresponding to NA coding or noncoding sequences for vRNA production and sequences for mRNA production of NA.

Further provided are methods of using vectors and compositions of the invention, e.g., to prepare a vaccine. In one embodiment, the present invention provides for live, attenuated vaccines for H5 viruses. Attenuation may be achieved by deleting NA gene segment and/or introducing attenuating genes or mutations. Moreover, as described herein, a HA associated with virulence can be 'detoxified' by replacing a multi-basic HA cleavage site with a single basic residue, and this modified HA gene can be employed to generate NA-deficient H5 viruses containing an avirulent-type HA cleavage sequence. Other attenuating mutations may be introduced, e.g., those in cold adapted influenza virus. In one embodiment, the invention provides a method to prepare attenuated, 7 segment influenza A or B virus. The method includes contacting a cell with one or more vectors which include transcription cassettes for vRNA production and transcription cassettes for mRNA production. The transcription cassettes for vRNA production include a transcription cassette having a promoter operably linked to an influenza virus PA cDNA linked to a transcription termination sequence, a transcription cassette having a promoter operably linked to an influenza virus PB1 cDNA linked to a transcription termination sequence, a transcription cassette having a promoter operably linked to an influenza virus PB2 cDNA linked to a transcription termination sequence, a transcription cassette having a promoter operably linked to an influenza virus HA cDNA linked to a transcription termination sequence, a transcription cassette having a promoter operably linked to an influenza virus NP cDNA linked to a transcription termination sequence, a transcription cassette having a promoter operably linked to an influenza virus M cDNA linked to a transcription termination sequence, and a transcription cassette having a promoter operably linked to an influenza virus NS cDNA linked to a transcription termination sequence. The transcription cassettes for mRNA production include a transcription cassette having a promoter operably linked to a DNA coding region for influenza virus PA linked to a transcription termination sequence, a transcription cassette having a promoter operably linked to a DNA coding region for influenza virus PB1 linked to a transcription termination sequence, a transcription cassette having a promoter operably linked to a DNA coding region for influenza virus PB2 linked to a transcription termination sequence, and/or a transcription cassette having a promoter operably linked to a DNA coding region for influenza virus NP linked to a transcription termination sequence. The cell is not contacted with sequences corresponding to NA coding or noncoding sequences for vRNA production, or with sequences corresponding to NA coding or noncoding sequences for vRNA production and sequences for mRNA production of NA.

In one embodiment the invention provides a method to prepare attenuated, 7 segment influenza A or B virus. The method includes contacting a cell with one or more vectors which include transcription cassettes for vRNA production. In one embodiment, the transcription cassette includes a transcription cassette having a PolI promoter operably linked to an influenza virus PA cDNA linked to a PolI transcription termination sequence, a transcription cassette having a PolI promoter operably linked to an influenza virus PB1 cDNA linked to a PolI transcription termination sequence, a transcription cassette having a PolI promoter operably linked to an influenza virus PB2 cDNA linked to a PolI transcription termination sequence, a transcription cassette having a PolI promoter operably linked to an influenza virus HA cDNA linked to a PolI transcription termination sequence, a transcription cassette having a PolI promoter operably linked to an influenza virus NP cDNA linked to a PolI transcription termination sequence, a transcription cassette having a PolI promoter operably linked to an influenza virus M cDNA linked to a PolI transcription termination sequence, and a transcription cassette having a PolI promoter operably linked to an influenza virus NS cDNA linked to a PolI transcription termination sequence. The cell is not contacted with sequences corresponding to NA coding or noncoding sequences for vRNA production, or with sequences corresponding to NA coding or noncoding sequences for vRNA production and sequences for mRNA production of NA.

BRIEF DESCRIPTION OF THE DRAWINGS

FIG. 5. Virulence and tissue tropism of VN1194$NA^-$ virus. The $MLD_{50}$ was determined as described in the Materials and Methods. BALB/c mice, anesthetized with isoflurane, were immunized intranasally with 50 μL of virus (100 pfu for VN1194 and $1\times10^5$ pfu for VN1194NA−). Three mice were sacrificed on day 3 and day 6 after immunization for virus titration. When virus was not recovered from all three mice, individual titers were recorded.

FIG. 8 Virus titers at day 3 in $NA^-$ influenza virus immunized mice challenged with VN1194 (H5N1), VN1203 (H5N1) or Indonesia7 (H5N1). Six mice from each group were sacrificed on day 3 post-challenge for virus titration. When virus was not recovered from all 6 mice, individual titers were recorded.

FIG. 9. Virus titers at day 6 in $NA^-$ influenza virus immunized mice challenged with VN1194 (H5N1), VN1203 (H5N1) or Indonesia7 (H5N1). Six mice from each group were sacrificed on day 6 post-challenge for virus titration. When virus was not recovered from all 6 mice, individual titers were recorded.

DETAILED DESCRIPTION OF THE INVENTION

Definitions

Figure 1:
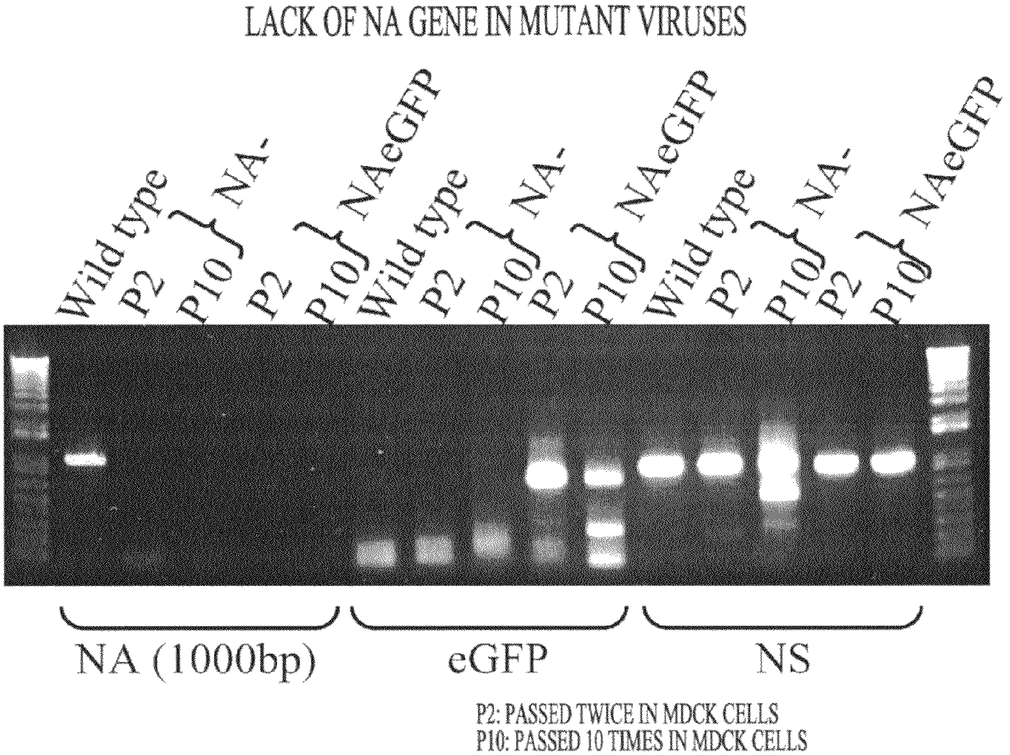
FIG. 1. Analysis of NA, GFP and NS gene segments in $NA^-$, NAeGFP and wild-type influenza virus.

As used herein, the terms "isolated" refers to in vitro preparation, isolation of a nucleic acid molecule such as a vector or plasmid of the invention or a virus of the invention, so that it is not associated with in vivo substances, or is substantially purified from in vitro substances. An isolated virus preparation is generally obtained by in vitro culture and propagation and is substantially free from other infectious agents. As used herein, "substantially free" means below the level of detection for a particular infectious agent using standard detection methods for that agent. A "recombinant" virus is one which has been manipulated in vitro, e.g., using recombinant DNA techniques, to introduce changes to the viral genome, e.g., deletion of sequences or entire gene segments, or otherwise artificially generated. As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Negative-Sense RNA Viruses

Negative-sense RNA viruses are classified into seven families (Rhabdoviridae, Paramyxoviridae, Filoviridae, Bornaviridae, Orthomyxoviridae, Bunyaviridae, and Arenaviridae) which include common human pathogens, such as respiratory syncytial virus, influenza virus, measles virus, and Ebola virus, as well as animal viruses with major economic impact on the poultry and cattle industries (e.g., Newcastle disease virus and Rinderpest virus). The first four families are characterized by nonsegmented genomes, while the latter three have genomes comprised of six-to-eight, three, or two negative-sense RNA segments, respectively. The common feature of negative-sense RNA viruses is the negative polarity of their RNA genome; i.e., the viral RNA (vRNA) is complementary to mRNA and therefore is not infectious by itself. In order to initiate viral transcription and replication, the vRNA has to be transcribed into a plus-sense mRNA or cRNA, respectively, by the viral polymerase complex and the nucleoprotein; for influenza A viruses, the viral polymerase complex is comprised of the three polymerase proteins PB2, PB1, and PA. During viral replication, cRNA serves as a template for the synthesis of new vRNA molecules. For all negative-stranded RNA viruses, non-coding regions at both the 5' and 3' termini of the vRNA and cRNA are critical for transcription and replication of the viral genome. Unlike cellular or viral mRNA transcripts, both cRNA and vRNA are neither capped at the 5' end nor polyadenylated at the very 3' end.

The basic functions of many viral proteins have been elucidated biochemically and/or in the context of viral infection. However, reverse genetics systems have dramatically increased our knowledge of negative-stranded segmented and non-segmented RNA viruses with respect to their viral replication and pathogenicity, as well as to the development of live attenuated virus vaccines. Reverse genetics, as the term is used in molecular virology, is defined as the generation of virus possessing a genome derived from cloned cDNAs (for a review, see Neumann et al., 2002).

Influenza viruses are orthomyxoviruses. Influenza A viruses possess a genome of eight single-stranded negative-sense viral RNAs (vRNAs) that encode a total of ten to eleven proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, the M segment of influenza B virus encodes two proteins, M1 and BM2, through a termination-reinitiation scheme of tandem cistrons, and the NA segment encodes the NA and NB proteins from a bicistronic mRNA. Influenza C virus, which has 7 vRNA segments, relies on spliced transcripts to produce M1 protein; the product of the unspliced mRNA is proteolytically cleaved to yield the CM2 protein. In addition, influenza C virus encodes a HA-esterase ("HEF") rather than individual HA and NA proteins.

Influenza Vaccines

Current vaccines for seasonal influenza are trivalent—they contain two influenza A virus strains of the H3N2 and H1N1 subtypes and an influenza B virus. On average, these vaccines are updated every 2-3 years due to accumulated point mutations in the HA and NA proteins that allow the viruses to evade the human immune response. Current influenza vaccines are either inactivated or live attenuated vaccines. Inactivated vaccines dominate the influenza virus vaccine market and are made from reassortant viruses that contain genes encoding the surface proteins of the predominant or targeted strain, most notably the HA gene and the NA gene. These viruses are typically overproduced in chicken eggs and then chemically treated, e.g., with formaldehyde, to inactivate them. The introduction of the inactivated but intact virions induces an immune response specific for the combination of HA and NA (also referred to as H and N, e.g., H5N1).

Until recently, inactivated virus preparations were the only influenza vaccines available. Most inactivated vaccines are safe and elicit a humoral, but not a strong cellular, immune response. To produce seed strains, embryonated chicken eggs are co-infected with the epidemic strain and A/Puerto Rico/8/34(H1N1) (PR8) virus, which provides high-growth properties. For influenza B virus vaccine production, a field strain is used to provide the virus backbone. Virus populations are screened for reassortants that contain the HA and NA genes of the epidemic strain and grow well in eggs. Once an appropriate vaccine seed virus is selected, it is amplified in eggs, purified, and treated to generate inactivated, split (i.e., disrupted), or subunit (i.e., partially purified by the removal of viral ribonucleoprotein complexes) vaccines. Vaccine quantities are then standardized and adjusted to 15 μg HA per strain.

The efficacy of inactivated influenza vaccines typically ranges from 60% to 90% in healthy adults younger than 65 years of age (Beyer et al., 2002). It can, however, be significantly lower in young children (Smith et al., 2006) due to their naive immune status and in the elderly (Gross et al., 1995; Nichol et al., 1998) due to their decreased immune function, thus leaving two major risk groups partially unprotected.

Live but attenuated vaccines are more controversial because they involve live virus which is shed by the patient for several weeks, although they elicit both humoral and cellular immune responses. This live virus contains mutations such that while it can replicate, it is not supposed to be virulent, i.e., is not supposed to cause flu.

Attenuated influenza virus vaccine has been developed by gradual cold-adaptation of influenza A/Ann Arbor/6/60 (H2N2) and B/Ann Arbor/1/66 viruses (Maassab et al., 1999). Both viruses contain mutations in several genes that determine cold-adaptation, temperature-sensitivity, and/or attenuation (Chen et al., 2006; Hoffmann et al., 2005; Jin et al., 2003; Jin et al., 2004). For vaccine production, eggs are co-infected with the attenuated vaccine strain and an epidemic strain. A reassortant is selected that contains the HA and NA genes of the epidemic strain and the 6 remaining genes of the live attenuated virus. This so-called 6+2 reassortant is amplified in eggs and administered intranasally. This live, attenuated influenza virus vaccine is stable, safe, and immunogenic in healthy adults. However, its use is restricted to persons 5-to-49 years of age, suggesting that it may not be sufficiently attenuated, especially for the elderly.

Reverse Genetic Technologies for Influenza Vaccine Production

The production of both inactivated and live influenza vaccines relies on the isolation of reassortant viruses with certain gene constellations. The co-infection of cells with two different influenza A or B viruses yields $2^8=256$ different gene combinations, making the isolation of the desired reassortant cumbersome. In 1999, a system was developed that allows the artificial generation of influenza viruses from cloned cDNA (Neumann et al., 1999). In this approach, cells are co-transfected with plasmids that encode the influenza vRNAs and plasmids that encode the components of the viral replication complex (i.e., the polymerase and NP proteins). The former plasmids contain a promoter for vRNA production, e.g., an RNA polymerase I promoter sequence, a cDNA encoding a full-length viral RNA in the negative-sense orientation, and a RNA terminator sequence, e.g., an RNA polymerase I terminator sequence. Intracellular transcription by RNA polymerase I yields transcripts identical to influenza viral RNAs that can therefore be amplified by the viral polymerase and nucleoproteins. Forty-eight hours post-transfection, up to $10^8$ infectious viruses are detected per ml of cell culture supernatant. This system allows the introduction of any (viable) mutation into the influenza viral genome. Moreover, tailor-made reassortant viruses can be generated using this system. To produce vaccine viruses, cells can be transfected with 2 plasmids encoding the HA and NA genes of the epidemic strain and 6 plasmids encoding the internal genes of either PR8 virus (for the production of inactivated vaccine) or attenuated A/Ann Arbor/6/60 virus (for the production of live attenuated virus). As described herein, reverse genetics is the basis for the development of live, attenuated influenza virus vaccines that lack NA activity and optionally contain mutations in other viral genes, e.g., mutations in the HA gene that reduce the pathogenic potential of the resulting virus.

The amino acid composition at the HA cleavage site is recognized as a determinant of virulence for influenza viruses (Bosch et al., 1979). HPAI influenza viruses contain multiple basic amino acids at their HA cleavage site (Kawaoka et al., 1984) that are recognized by ubiquitous cellular proteases (Horimoto et al., 1997; Stieneke-Grober et al., 1998), which leads to systemic infection. By contrast, viruses with low pathogenicity contain a single arginine residue at the HA cleavage site (Kawaoka et al., 1984), which is cleaved in only a few organs, resulting in localized infection. Multiple basic amino acids at the HA cleavage site may be associated with virulence, as replacement of the 'virulent-type' HA cleavage site with an 'avirulent-type' HA cleavage site converted a highly pathogenic avian influenza virus into a low pathogenic variant (Horimoto et al., 1990). Thus, highly pathogenic avian influenza viruses can be converted to low pathogenic forms by replacing the 'virulent-type' HA cleavage sequence with an 'avirulent-type' sequence (Horimoto et al., 1994). These 'detoxifying' mutations can be introduced into viral genomes to generate candidate vaccines that contain attenuated H5 virus HA genes in a background of, for example, high-growth PR8 virus.

Exemplary Vectors of the Invention

In one embodiment, the invention provides one or more isolated vectors, or a composition which includes one or more isolated vectors, having a plurality of transcription cassettes: one or more vectors having a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus M cDNA, e.g., a full-length influenza virus M cDNA, linked to a PolI transcription termination sequence, a transcription cassette comprising a PolI promoter operably linked to an influenza virus NS cDNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence, and optionally one or more of the following: a transcription cassette comprising a PolII promoter and a PolII transcription termination operably linked to a DNA segment for influenza virus HA, e.g., a full-length influenza virus HA cDNA, a transcription cassette comprising a PolII promoter and a PolII transcription termination sequence operably linked to a DNA segment for influenza virus M, e.g., a full-length influenza virus M cDNA, and/or a transcription cassette comprising a PolII promoter sequence and a PolII transcription termination sequence operably linked to a DNA segment for influenza virus NS, e.g., a full-length influenza virus NS cDNA.

In one embodiment, a vector of the invention may include two or more transcription cassettes selected from a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HA cDNA, e.g., a full-length HA cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus NS cDNA, e.g., a full-length influenza virus NS cDNA, linked to a PolI transcription termination sequence, and a transcription cassette comprising a PolI promoter operably linked to an influenza virus M cDNA, e.g., a full-length influenza virus M cDNA, linked to a PolI transcription termination sequence.

In one embodiment, a vector of the invention includes two or more transcription cassettes selected from a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and a transcription cassette comprising a PolII promoter operably linked to a DNA coding region for influenza virus NP linked to a PolII transcription termination sequence.

The invention further includes a vector with at least two transcription cassettes selected from a transcription cassette comprising a PolI promoter and a PolI transcription termination sequence and a PolII promoter and a PolII transcription termination sequence each operably linked to a DNA segment for influenza virus PA, e.g., a full-length influenza virus PA cDNA, a transcription cassette comprising a PolI promoter and a PolI transcription termination sequence and a PolII promoter and a PolII transcription termination sequence each operably linked to a DNA segment for influenza virus PB1, e.g., a full-length influenza virus PB1 cDNA, a transcription cassette comprising a PolI promoter and a PolI transcription termination sequence and a PolI promoter and a PolII transcription termination sequence each operably linked to a DNA segment for influenza virus PB2, e.g., a full-length influenza virus PB2 cDNA, and/or a transcription cassette comprising a PolI promoter and a PolI transcription termination sequence and a PolII promoter and a PolII transcription termination sequence each operably linked to a DNA segment for influenza virus NP, e.g., a full-length influenza virus NP cDNA.

The invention also provides one or more isolated vectors having a plurality of transcription cassettes: one or more vectors having a transcription cassette comprising a PolII promoter linked to a ribozyme sequence linked to an influenza virus PA cDNA, e.g., a full-length influenza virus PA cDNA, linked to a ribozyme sequence linked to a PolII transcription termination sequence, a transcription cassette comprising a PolII promoter linked to a ribozyme sequence linked to an influenza virus PB1 cDNA, e.g., a full-length influenza virus PB1 cDNA, linked to a ribozyme sequence linked to a PolII transcription termination sequence, a transcription cassette comprising a PolII promoter linked to a ribozyme sequence linked to an influenza virus PB2 cDNA, e.g., a full-length influenza virus PB2 cDNA, linked to a ribozyme sequence linked to a PolII transcription termination sequence, a transcription cassette comprising a PolII promoter linked to a ribozyme sequence linked to an influenza virus HA cDNA, e.g., a full-length influenza virus HA cDNA, linked to a ribozyme sequence linked to a PolII transcription termination sequence, a transcription cassette comprising a PolII promoter linked to a ribozyme sequence linked to an influenza virus NP cDNA, e.g., a full-length influenza virus NP cDNA, linked to a ribozyme sequence linked to a PolII transcription termination sequence, a transcription cassette comprising a PolII promoter linked to a ribozyme sequence linked to an influenza virus M cDNA, e.g., a full-length influenza virus M cDNA, linked to a ribozyme sequence linked to a PolII transcription termination sequence, a transcription cassette comprising a PolII promoter linked to a ribozyme sequence linked to an influenza virus NS cDNA, e.g., a full-length influenza virus NS cDNA, linked to a ribozyme sequence linked to a PolII transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence, and optionally one or more of the following: a transcription cassette comprising a PolII promoter and a PolII transcription termination operably linked to a DNA segment for influenza virus HA, e.g., a full-length influenza virus HA cDNA, a transcription cassette comprising a PolII promoter and a PolII transcription termination sequence operably linked to a DNA segment for influenza virus M, e.g., a full-length influenza virus M cDNA, and/or a transcription cassette comprising a PolII promoter sequence and a PolII transcription termination sequence operably linked to a DNA segment for influenza virus NS, e.g., a full-length influenza virus NS cDNA.

In one embodiment, the use of certain plasmid vectors significantly reduces the number of plasmids required for the generation of segmented virus such as influenza virus, increases the rescue efficiency of influenza virus in cell lines that can be transfected with high efficiencies, allowing the generation of viruses that are severely attenuated, and/or allowing for the generation of influenza virus in cell lines that cannot be transfected with high efficiencies, including cell lines for the production of human vaccines (e.g., Vero cells). Accordingly, the use of the vectors of the invention reduces the number of variables for virus generation, resulting in more consistent generation of influenza virus, and decreasing the burden of providing proper documentation of plasmid history, purity, and toxicity. These advantages allow the speedy generation of vaccine viruses, especially for pandemics.

Exemplary Compositions of the Invention

The invention provides a composition comprising at least one vector, e.g., at least one plasmid, which includes two or more transcription cassettes for vRNA production selected from a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus M cDNA, e.g., a full-length influenza virus M cDNA, linked to a PolI transcription termination sequence, and/or a transcription cassette comprising a PolI promoter operably linked to an influenza virus NS cDNA, e.g., a full-length influenza virus NS cDNA, linked to a PolI transcription termination sequence; and at least one vector, e.g., at least one plasmid, which includes one or more transcription cassettes for mRNA production selected from a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence. In one embodiment, each PolI promoter is the same. In one embodiment, each PolII promoter is the same. In one embodiment, each PolI transcription terminator sequence is the same. In one embodiment, each PolII transcription terminator sequence is the same.

In one embodiment, at least one plasmid for vRNA production includes transcription cassettes for one or more of influenza virus PA, influenza virus PB1, influenza virus PB2, influenza virus HA, influenza virus NP, influenza virus M, and influenza virus NS segments. In one embodiment, at least one plasmid for mRNA production includes transcription cassettes for one or more of influenza virus PA, influenza virus PB1, influenza virus PB2 or influenza virus NP, e.g., the at least one plasmid for mRNA production includes cassettes for influenza virus PA, influenza virus PB1, influenza virus PB2 and influenza virus NP. In one embodiment, one plasmid for mRNA production includes three of the cassettes, wherein the composition further comprises another plasmid for mRNA production with a PolII promoter operably linked to a DNA coding region for an influenza virus gene linked to a PolII transcription termination sequence. For instance, one plasmid for mRNA production includes transcription cassettes for influenza virus PA, influenza virus PB1, influenza virus PB2 and another plasmid includes a transcription cassette for influenza virus NP. In another embodiment, at least one plasmid for vRNA production includes transcription cassettes for influenza virus PA, influenza virus PB1, influenza virus PB2, influenza virus NP, influenza virus M, and influenza virus NS. Also included is a plasmid for vRNA production which includes a transcription cassette comprising a PolI promoter operably linked to an influenza virus HA cDNA, e.g., a full-length influenza virus HA cDNA, linked to a PolI transcription termination sequence. For instance, one plasmid for mRNA production includes cassettes for influenza virus PA, influenza virus PB1, influenza virus PB2 and influenza virus NP. In another embodiment, one plasmid for mRNA production includes three of the cassettes, wherein the composition further comprises another plasmid for mRNA production with a PolII promoter operably linked to a DNA coding region for an influenza virus gene linked to a PolII transcription termination sequence, wherein the DNA coding region is for an influenza virus gene that is not on the plasmid which includes the three cassettes, e.g., the at least one plasmid for mRNA production includes cassettes for influenza virus PA, influenza virus PB1, influenza virus PB2 and the other plasmid includes a cassette for influenza virus NP.

In one embodiment, a composition of the invention comprises a plasmid which includes a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus M cDNA, e.g., a full-length influenza virus M cDNA, linked to a PolI transcription termination sequence, and a transcription cassette comprising a PolI promoter operably linked to an influenza virus NS cDNA, e.g., a full-length influenza virus NS cDNA, linked to a PolI transcription termination sequence. In one embodiment, the HA in a transcription cassette is a type A HA. In another embodiment, the HA in a transcription cassette is a type B HA. In one embodiment, the RNA polymerase I promoter is a human RNA polymerase I promoter. In one embodiment, the composition includes transcription cassettes comprising a PolI promoter operably linked to an influenza virus DNA sequence for M1 and BM2 or for both M1 and M2, linked to a PolI transcription termination sequence.

Also provided a composition comprising a plasmid which includes two or more transcription cassettes selected from a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence.

In another embodiment, the invention provides a composition comprising a plasmid which includes one or more transcription cassettes selected from a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus M cDNA, e.g., a full-length influenza virus M cDNA, influenza virus linked to a PolI transcription termination sequence, and a transcription cassette comprising a PolI promoter operably linked to an influenza virus NS cDNA, e.g., a full-length influenza virus NS cDNA, linked to a PolI transcription termination sequence; and one or more transcription cassettes selected from a transcription cassette comprising a PolI promoter and a PolI transcription termination sequence and a PolII promoter and a PolII transcription termination sequence each operably linked to a cDNA for influenza virus PA, e.g., a full-length influenza virus PA cDNA, a transcription cassette comprising a PolI promoter and a PolI transcription termination sequence and a PolII promoter and PolII transcription termination sequence each operably linked to a cDNA for influenza virus PB1, e.g., a full-length influenza virus PB1 cDNA, a transcription cassette comprising a PolI promoter and a PolI transcription termination sequence and a PolII promoter and a PolII transcription termination sequence each operably linked to a cDNA for influenza virus PB2, e.g., a full-length influenza virus PB2 cDNA, and a transcription cassette comprising a PolI promoter and a PolI transcription termination sequence and a PolII promoter and a PolII transcription termination sequence each operably linked to a cDNA for influenza virus NP, e.g., a full-length influenza virus NP cDNA. In one embodiment, the HA in a transcription cassette is a type A HA. In another embodiment, the HA in a transcription cassette is a type B HA. In one embodiment, the RNA PolI promoter is a human RNA PolI promoter. In one embodiment, the composition further includes a transcription cassette comprising a PolI promoter operably linked to an influenza virus M cDNA, e.g., one having M1 and BM2, linked to a PolI transcription termination sequence.

Further provided is a composition comprising a plasmid which includes a transcription cassette comprising a PolI promoter and a PolI transcription termination sequence and a PolII promoter and a PolII transcription termination sequence each operably linked to a cDNA for influenza virus PA, e.g., a full-length influenza virus PA, a transcription cassette comprising a PolI promoter and a PolI transcription termination sequence and a PolII promoter and PolII transcription termination sequence each operably linked to a cDNA for influenza virus PB1, e.g., a full-length influenza virus PB1 cDNA, a transcription cassette comprising a PolI promoter and a PolI transcription termination sequence and a PolII promoter and a PolII transcription termination sequence each operably linked to a cDNA for influenza virus PB2, e.g., a full-length influenza virus PB2 cDNA, and a transcription cassette comprising a PolI promoter and a PolI transcription termination sequence and a PolII promoter and a PolII transcription termination sequence each operably linked to a cDNA for influenza virus NP, e.g., a full-length influenza virus NP cDNA.

The compositions of the invention may include vectors with influenza virus sequences having one or more additional mutations (in addition to the NA-mutation) including additional attenuating mutations. For example, additional attenuating mutations may be desirable for some recombinant human influenza viruses employed in vaccines, e.g., for H5 viruses including $HA_{Av}$ viruses. For example, additional mutations may include, but are not limited to, a substitution in the HA cleavage site, a substitution in or a deletion in the transmembrane (TM) domain of M2 (see U.S. Pat. No. 6,872,395 and U.S. application Ser. No. 60/944,680), e.g., for influenza A virus, substitutions may be at any one or more of residues 25 to 43 in the TM domain of M2, for instance, at positions 27, 30, 31, 34, 38, and/or 41 of the TM domain of M2 (for example, a V27T, A30P, S31N, or W41A substitution), or a deletion in the TM domain of M2, for instance, a deletion of at least residue 29, 30 or 31, or any combination thereof, in the TM domain of M2, a deletion in the cytoplasmic tail of M2, e.g., including a deletion of 2 or more residues and up to 21 residues of the cytoplasmic tail of M2, such as a deletion of the 11 C-terminal amino acids of the M2 cytoplasmic tail, or one or more substitutions associated with temperature sensitivity (e.g., cold adapted viruses), such as substitutions in PB1, e.g., K391E, E581G, or A661T, substitutions in PB2, e.g., N265S, and/or substitutions in NP, e.g., D34G (see Jin et al., *Virology,* 306:18 (2003)).

Exemplary Methods

The invention also provides a method to prepare an attenuated influenza virus. The method includes contacting a cell with a vector such as a plasmid which includes one or more transcription cassettes selected from a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, and/or a transcription cassette comprising a PolI promoter operably linked to an influenza virus M cDNA, e.g., a full-length influenza virus M cDNA, linked to a PolI transcription termination sequence and/or a transcription cassette comprising a PolI promoter operably linked to an influenza virus NS cDNA, e.g., a full-length influenza virus NS cDNA, linked to a PolI transcription termination sequence; and a plasmid which includes one or more transcription cassettes selected from a transcription cassette, a transcription cassette comprising a PolII promoter operably linked to a DNA coding region for influenza virus PA, a transcription cassette comprising a PolII promoter operably linked to a DNA coding region for influenza virus PB1, a transcription cassette comprising a PolII promoter operably linked to a DNA coding region for influenza virus PB2, and/or a transcription cassette comprising a PolII promoter operably linked to a DNA coding region for influenza virus NP.

In one embodiment, a method to prepare an attenuated influenza virus includes contacting a cell with a plasmid which includes a transcription cassette comprising a PolI promoter operably linked to an influenza virus HA cDNA, e.g., a full-length influenza virus HA cDNA, linked to a PolI transcription termination sequence, a transcription cassette comprising a promoter operably linked to an influenza virus M cDNA, e.g., a full-length influenza virus M cDNA, linked to a PolI transcription termination sequence, a transcription cassette comprising a PolI promoter operably linked to an influenza virus NS cDNA, e.g., a full-length influenza virus NS cDNA, linked to a PolI transcription termination sequence, and optionally includes one or more transcription cassettes selected from a transcription cassette comprising a PolI promoter and a PolI transcription termination sequence and a PolII promoter and a PolII transcription termination sequence each operably linked to a cDNA for influenza virus PA, e.g., a full-length influenza virus PA cDNA, a transcription cassette comprising a PolI promoter and a PolI transcription termination sequence and a PolII promoter and a PolII transcription termination sequence each operably linked to a cDNA for influenza virus PB1, e.g., a full-length influenza virus PB1 cDNA, a transcription cassette comprising a PolI promoter and a PolI transcription termination sequence and a PolI promoter and a PolII transcription termination sequence each operably linked to a cDNA for influenza virus PB2, e.g., a full-length influenza virus PB2 cDNA, and/or a transcription cassette comprising a PolI promoter and a PolI transcription termination sequence and a PolII promoter and a PolII transcription termination sequence each operably linked to a cDNA for influenza virus NP e.g., a full-length influenza virus NP cDNA.

In one embodiment, the method of the invention includes contacting a cell with one or more vectors comprising a transcription cassette comprising a promoter linked to 5' influenza virus sequences comprising 5' influenza virus non-coding sequences and optionally adjacent portions of the coding sequence (see PCT/US03/04233, which is incorporated by reference herein), linked to a DNA of interest linked to 3' influenza virus sequences comprising 3' influenza virus noncoding sequences and optionally adjacent portions of the coding sequence, linked to a transcription termination sequence (see PCT/US03/04233). In one embodiment, the DNA of interest is in the sense orientation. In another embodiment, the DNA of interest is in the negative sense orientation. The DNA of interest may include an open reading frame encoding an immunogenic polypeptide or peptide of a pathogen or a therapeutic polypeptide or peptide. The DNA of interest may be operably linked to a PolI promoter and a PolI transcription termination sequence, and/or the DNA of interest is operably linked to a PolII promoter and a PolII transcription termination sequence.

The methods of the invention may be employed to prepare recombinant influenza viruses. In one embodiment, the methods include the use of vectors with influenza virus sequences having one or more additional mutations (in addition to the NA− mutation) including additional attenuating mutations. For example, additional attenuating mutations may be desirable for some recombinant human influenza viruses employed in vaccines, e.g., for H5 viruses including $HA_{Av}$ viruses. For example, additional mutations may include, but are not limited to, a substitution in the HA cleavage site, a substitution in or a deletion in the transmembrane (TM) domain of M2 (see U.S. Pat. No. 6,872,395 and U.S. application Ser. No. 60/944,680), e.g., for influenza A virus, substitutions may be at any one or more of residues 25 to 43 in the TM domain of M2, for instance, at positions 27, 30, 31, 34, 38, and/or 41 of the TM domain of M2 (for example, a V27T, A30P, S31N, or W41A substitution), or a deletion in the TM domain of M2, for instance, a deletion of at least residue 29, 30 or 31, or any combination thereof, in the TM domain of M2, a deletion in the cytoplasmic tail of M2, e.g., including a deletion of 2 or more residues and up to 21 residues of the cytoplasmic tail of M2, such as a deletion of the 11 C-terminal amino acids of the M2 cytoplasmic tail, or one or more substitutions associated with temperature sensitivity (e.g., cold adapted viruses), such as substitutions in PB1, e.g., K391E, E581G, or A661T, substitutions in PB2, e.g., N265S, and/or substitutions in NP, e.g., D34G (see Jin et al., *Virology,* 306:18 (2003)).

Cell Lines and Influenza Viruses That Can Be Used in the Present Invention

According to the present invention, any cell which supports efficient replication of influenza virus can be employed in the invention, including mutant cells which express reduced or decreased levels of one or more sialic acids which are receptors for influenza virus. Viruses obtained by the methods can be made into a reassortant virus.

Preferably, the cells are WHO certified, or certifiable, continuous cell lines, e.g., vero cells. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity is preferably tested in cells that are at the same passage level as those used for vaccine production. The vaccine virus is preferably purified by a process that has been shown to give consistent results (see, e.g., World Health Organization, 1982).

It is preferred to establish a complete characterization of the cell lines to be used, so that appropriate tests for purity of the final product can be included. Data that can be used for the characterization of a cell to be used in the present invention includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. Preferably, the passage level, or population doubling, of the host cell used is as low as possible.

It is preferred that the virus produced in the cell is highly purified prior to vaccine or gene therapy formulation. Generally, the purification procedures will result in the extensive removal of cellular DNA, other cellular components, and adventitious agents. Procedures that extensively degrade or denature DNA can also be used. See, e.g., Mizrahi, 1990.

Vaccines

A vaccine of the invention may comprise immunogenic proteins including glycoproteins of any pathogen, e.g., an immunogenic protein from one or more bacteria, viruses, yeast or fungi. Thus, in one embodiment, the influenza viruses of the invention may be vaccine vectors for influenza virus or other viral pathogens including but not limited to lentiviruses such as HIV, hepatitis B virus, hepatitis C virus, herpes viruses such as CMV or HSV or foot and mouth disease virus.

A complete virion vaccine is concentrated by ultrafiltration and then purified by zonal centrifugation or by chromatography. It is inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Webster et al., 1977); or a nonionic detergent such as that commercialized under the name TRITON X100. The hemagglutinin may also be isolated after treatment of the virions with a protease such as bromelin, then purified by a method.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

Inactivated Vaccines.

Inactivated influenza virus vaccines of the invention are provided by inactivating replicated virus of the invention using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines. In general, the responses to SV and surface antigen (i.e., purified HA or NA) vaccines are similar. An experimental inactivated WV vaccine containing an NA antigen immunologically related to the epidemic virus and an unrelated HA appears to be less effective than conventional vaccines (Ogra et al., 1977). Inactivated vaccines containing both relevant surface antigens are preferred.

Pharmaceutical Compositions

Pharmaceutical compositions of the present invention, suitable for inoculation or for parenteral or oral administration, comprise attenuated or inactivated influenza viruses, optionally further comprising sterile aqueous or non-aqueous solutions, suspensions, and emulsions. The compositions can further comprise auxiliary agents or excipients, as known in the art. See, e.g., Berkow et al., 1987*; Avery's Drug Treatment,* 1987. The composition of the invention is generally presented in the form of individual doses (unit doses).

Conventional vaccines generally contain about 0.1 to 200 μg, preferably 10 to 15 μg, of HA from each of the strains entering into their composition. The vaccine forming the main constituent of the vaccine composition of the invention may comprise a virus of type A, B or C, or any combination thereof, for example, at least two of the three types, at least two of different subtypes, at least two of the same type, at least two of the same subtype, or a different isolate(s) or reassortant(s). Human influenza virus type A includes H1N1, H2N2 and H3N2 subtypes.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents. See, e.g., Avery's, 1987.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized. Examples of materials suitable for use in vaccine compositions are provided.

Heterogeneity in a vaccine may be provided by mixing replicated influenza viruses for at least two influenza virus strains, such as 2-50 strains or any range or value therein. Influenza A or B virus strains having a modern antigenic composition are preferred. According to the present invention, vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines, are provided before any symptom of a pathogen infection becomes manifest. The prophylactic administration of the composition serves to prevent or attenuate any subsequent infection. The gene therapy compositions of the invention may be provided before any symptom of a disease becomes manifest. The prophylactic administration of the composition serves to prevent or attenuate one or more symptoms associated with the disease.

When provided therapeutically, an attenuated or inactivated viral vaccine is provided upon the detection of a symptom of actual infection. The therapeutic administration of the compound(s) serves to attenuate any actual infection. See, e.g., Avery, 1987. When provided therapeutically, a gene therapy composition is provided upon the detection of a symptom or indication of the disease. The therapeutic administration of the compound(s) serves to attenuate a symptom or indication of that disease.

Thus, an attenuated or inactivated vaccine composition of the present invention may thus be provided either before the onset of infection (so as to prevent or attenuate an anticipated infection) or after the initiation of an actual infection. Similarly, for gene therapy, the composition may be provided before any symptom of a disorder or disease is manifested or after one or more symptoms are detected.

A composition is said to be "pharmacologically acceptable" if its administration can be tolerated by a recipient patient. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of patients. Protection may be limited to mitigating the severity or rapidity of onset of symptoms of the influenza virus infection.

Pharmaceutical Administration

A composition of the present invention may confer resistance to one or more pathogens, e.g., one or more influenza virus strains, by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a symptom or condition of the disease, or in the total or partial immunity of the individual to the disease. As used herein, a gene therapy composition is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described.

For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. A preferred mode of using a pharmaceutical composition of the present invention is by intramuscular or subcutaneous application. See, e.g., Avery, 1987.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired biological effect. It is understood that the effective dosage will be dependent upon the age, sex, health, and weight of the recipient, kind of concurrent treatment, if any, frequency of treatment, and the nature of the effect wanted. The ranges of effective doses provided below are not intended to limit the invention and represent preferred dose ranges. However, the most preferred dosage will be tailored to the individual subject, as is understood and determinable by one of skill in the art. See, e.g., Avery's, 1987; and Ebadi, 1985.

The dosage of an attenuated virus vaccine for a mammalian (e.g., human) or avian adult organism can be from about $10^3$-$10^7$ plaque forming units (PFU)/kg, or any range or value therein. The dose of inactivated vaccine can range from about 0.1 to 200, e.g., 50 μg of hemagglutinin protein. However, the dosage should be a safe and effective amount as determined by conventional methods, using existing vaccines as a starting point.

The dosage of immunoreactive HA in each dose of replicated virus vaccine can be standardized to contain a suitable amount, e.g., 1-50 μg or any range or value therein, or the amount recommended by the U.S. Public Heath Service (PHS), which is usually 15 μg, per component for older children, 3 years of age, and 7.5 μg per component for older children <3 years of age. The quantity of NA can also be standardized, however, this glycoprotein can be labile during the processor purification and storage. Each 0.5-ml dose of vaccine preferably contains approximately 1-50 billion virus particles, and preferably 10 billion particles.

The invention will be further described by the following nonlimiting examples.

Example I

Characterization of a 7 Segment Influenza A Virus

NA-deficient viruses that lack the NA vRNA combine several attractive features: (i) high levels of attenuation; (ii) ease of generation by reverse genetics and (iii) biosafety, since there are no point mutations that may cause reversion to the wild-type phenotype. Moreover, reassortment of the 7 segment virus with a circulating wild-type strain would only re-create the wild-type strain from which the 7 segment virus was derived. Such a virus may be of particular interest for H5 and H3 influenza viruses. Although several candidate H5N1 virus vaccines have been developed (Bresson et al., 2006; Treanor et al., 2006), preclinical and clinical studies with inactivated subvirion or split vaccines have demonstrated that high doses of HA are needed to achieve adequate immune responses (Treanor et al., 2006). Even in the presence of adjuvant, 30 μg of HA were required to achieve an immune response equivalent to that typically found for non-adjuvanted H3 HA vaccines (Bresson et al., 2006).

Previously, viruses that lacked NA activity were prepared by passaging virus in the presence of an antibody to the NA molecule, while sialidase activity was provided by a cell line expressing NA or by exogenously applied bacterial sialidase. Both approaches resulted in viruses that contained large internal deletions in their NA genes. These NA-deficient viruses replicated in cell culture, eggs, and mice. Viruses deficient in NA may also be passaged in mutant cells such as those disclosed in U.S. application Ser. No. 10/081,170, e.g., MaKS cells, the disclosure of which is incorporated by reference herein, and Brandi et al., *J. Biol. Chem.,* 263:16283 (1988)).

Materials and Methods

Viruses.

Human H5N1 viruses [A/Vietnam/1203/2004 (VN1203) and A/Vietnam/1194/2004 (VN1204)] were used. Human isolates were grown in Madin-Darby canine kidney (MDCK) cells and maintained in minimal essential medium with 5% newborn calf serum. All experiments with live viruses and with transfectants generated by reverse genetics were performed in a biosafety level 3 containment laboratory approved for such use by the CDC and the U.S. Department of Agriculture.

Plasmid Construction and Reverse Genetics.

The cDNAs of the VN1194 and another human H5N1 virus A/Indonesia/7/2005 (Indonesia7) were synthesized by reverse transcription of viral RNA with an oligonucleotide (Uni 12) complementary to the conserved 3' end of the viral RNA, as described in Hatta et al. (2001). The cDNA was amplified by PCR with gene-specific oligonucleotide primers and then sequenced. The generation of plasmid constructs for viral RNA production (pPolI), and containing the genes of VN1194 and Indonesia7 viruses flanked by the human RNA polymerase I promoter and the mouse RNA polymerase I terminator, is described in Neumann et al. (1999). All constructs were sequenced to ensure the absence of unwanted mutations. Automated sequencing was performed at the University of Wisconsin-Madison Biotechnology Center. Transfectant viruses were produced by reverse genetics as described by Neumann et al. (1999). Experimental infection. The $MLD_{50}$, that is, the dose of virus lethal to 50% of mice, for the VN1194 and VN1194NA− viruses was determined by intranasal inoculation of anesthetized 4-week-old female BALB/c mice with 10-fold serial dilutions of virus. Infected mice were observed daily for 14 days. For virus titration in organs, mice were infected intranasally with 100 (VN1194) or $10^5$ PFU (VN1194NA−) of virus and euthanized on day 3 and day 6 post-infection as described in Gao et al. (1999).

To evaluate the protective efficacy of VN1194NA− against challenge with lethal doses of highly pathogenic H5N1 viruses, each mouse was infected intranasally with $10^5$ PFU of VN1194NA−. As a control, mice were inoculated intranasally with phosphate-buffered saline (PBS). Fourteen days later, serum samples, as well as trachea-lung and nasal washes, were collected from a subset of mice and examined for virus-specific immunoglobulin A (IgA) or G (IgG) antibodies, using VN1194 as an antigen, by use of an enzyme-linked immunosorbent assay (ELISA). On day 21 post-vaccination, the remaining mice were challenged intranasally with 100 $MLD_{50}$ of wild-type VN1194, VN1203, or Indonesia7 virus and monitored daily for survival and body weight for 14 days. Virus titers were determined in organs from six mice per group at 3 and 6 days post-challenge.

Results

A mutant A/Vietnam/1194/04 (H5N1) virus lacking the NA segment ("VN1194NA−") and a virus in which the NA segment was replaced with a mutant NA segment possessing an eGFP gene ("VN1194NAeGFP") were found to replicate in MDCK cells without exogenous neuraminidase treatment (Table 1).

TABLE 1

| Virus titers in MDCK cells |
|---|
| VN1194NA- P2 virus: $8.5 \times 10^5$ pfu/ml |
| VN1194NA- P10 virus: $4.3 \times 10^6$ pfu/ml |
| VN1194NAeGFP P2 virus: $2.3 \times 10^4$ pfu/ml |
| VN1194NAeGFP P10 virus: $3.0 \times 10^4$ pfu/ml |

Figure 2:
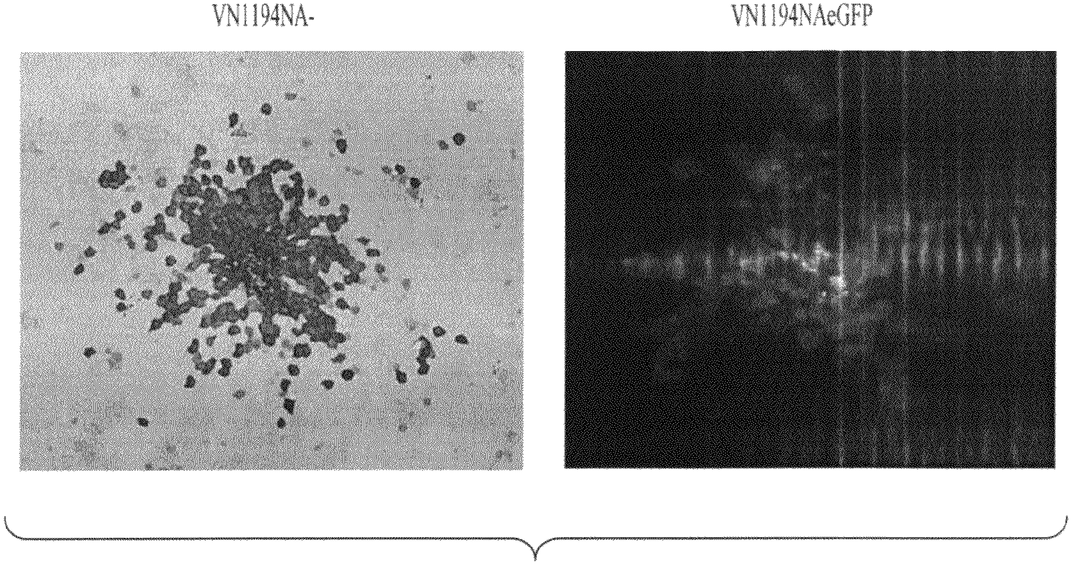
FIG. 2. MDCK cells infected with $NA^-$ and NAeGFP influenza viruses.
Figure 3:
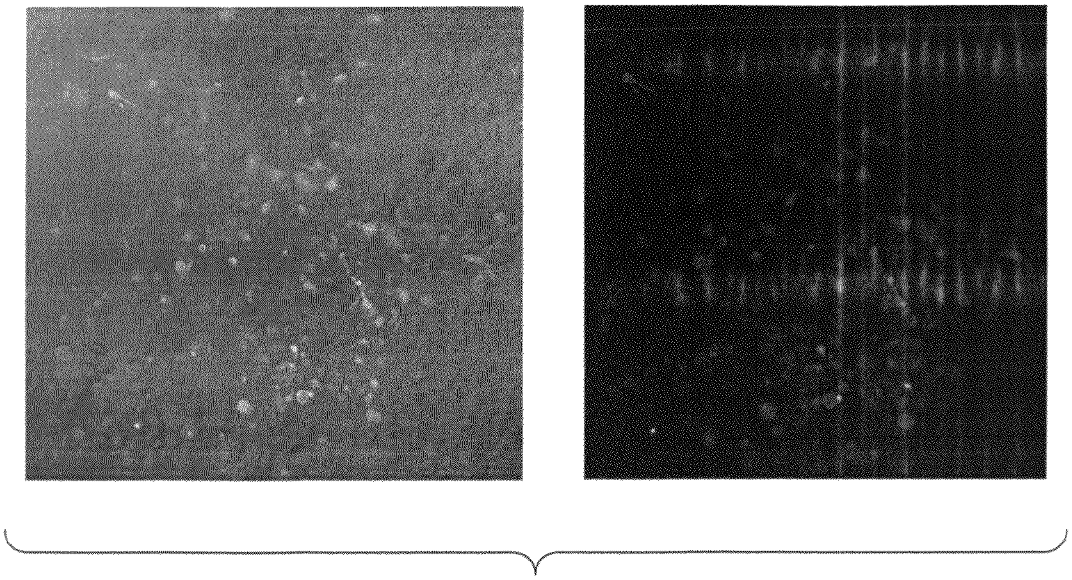
FIG. 3. Human nasal epithelial cells infected with $NA^-$ and NAeGFP influenza viruses.

The resulting viruses were characterized for the presence or absence of NA, eGFP or NS gene segments (FIG. 1). FIGS. 2 and 3 show images of MDCK or human nasal epithelial (HNE) cells infected with the viruses. The $MLD_{50}$ for the $VN1194NA^-$ virus in mice was $>10^5$ (P10: $4.3\times10^6$ pfu/ml) while that for wild-type virus was 3.1. The tissue tropism for $VN1194NA^-$ in mice is shown in FIG. 5. Wild type VN1194 virus was isolated from a variety of organs, including brain. VN1194NA− was isolated only from nasal turbinates, indicating that the VN1194NA− virus is attenuated in mice.

To test the $NA^-$ virus as a vaccine, Balb/c (4 week old, female) mice were immunized with VN1194NA− virus. Challenge viruses were VN1194 wild-type, A/Vietnam/1203/04, and A/Indonesia/7/05 (100 $LD_{50}$). The vaccination schedule was as follows, day 0, vaccination; days 3 and 6, organ sampling from 3 mice/group; day 14, serum, lung and NT wash collection (5 mice/group); day 21, challenge; days 24 and 27, organ sampling, 6 mice/group; from day 21 to day 35, weigh and morbidity check, 8 mice/group daily; and day 35, end.

Figure 4:
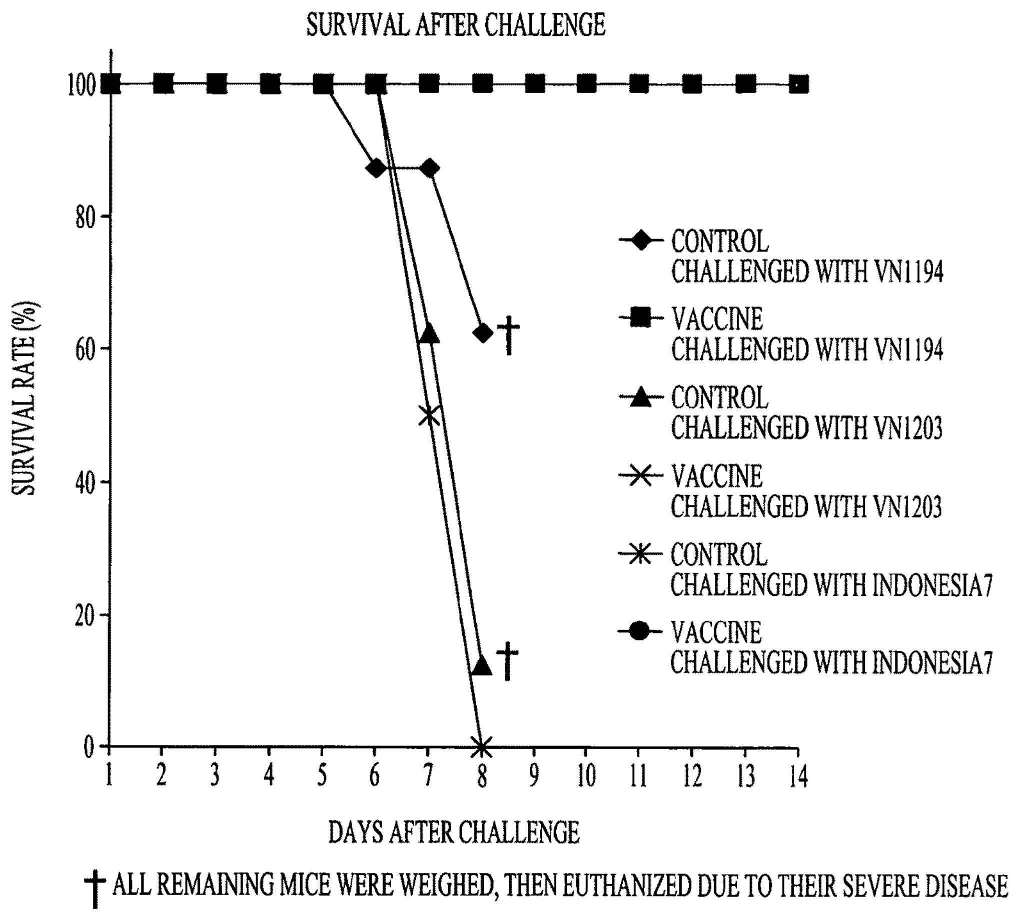
FIG. 4. Graph of survival rates versus day post challenge in control or $NA^-$ immunized mice challenged with VN1194 (H5N1), VN1203 (H5N1) or Indonesia 7 (H5N1).
Figure 6:
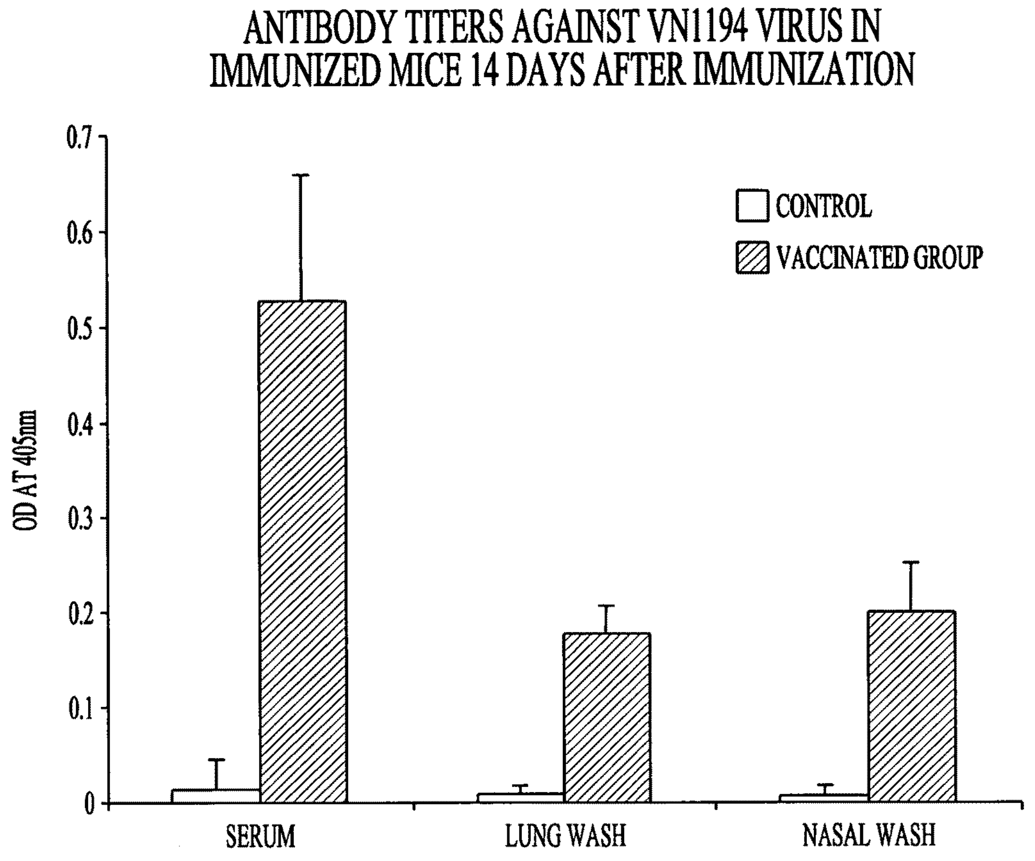
FIG. 6. Antibody titers against VN1194 virus in immunized mice 14 days after immunization.
Figure 7:
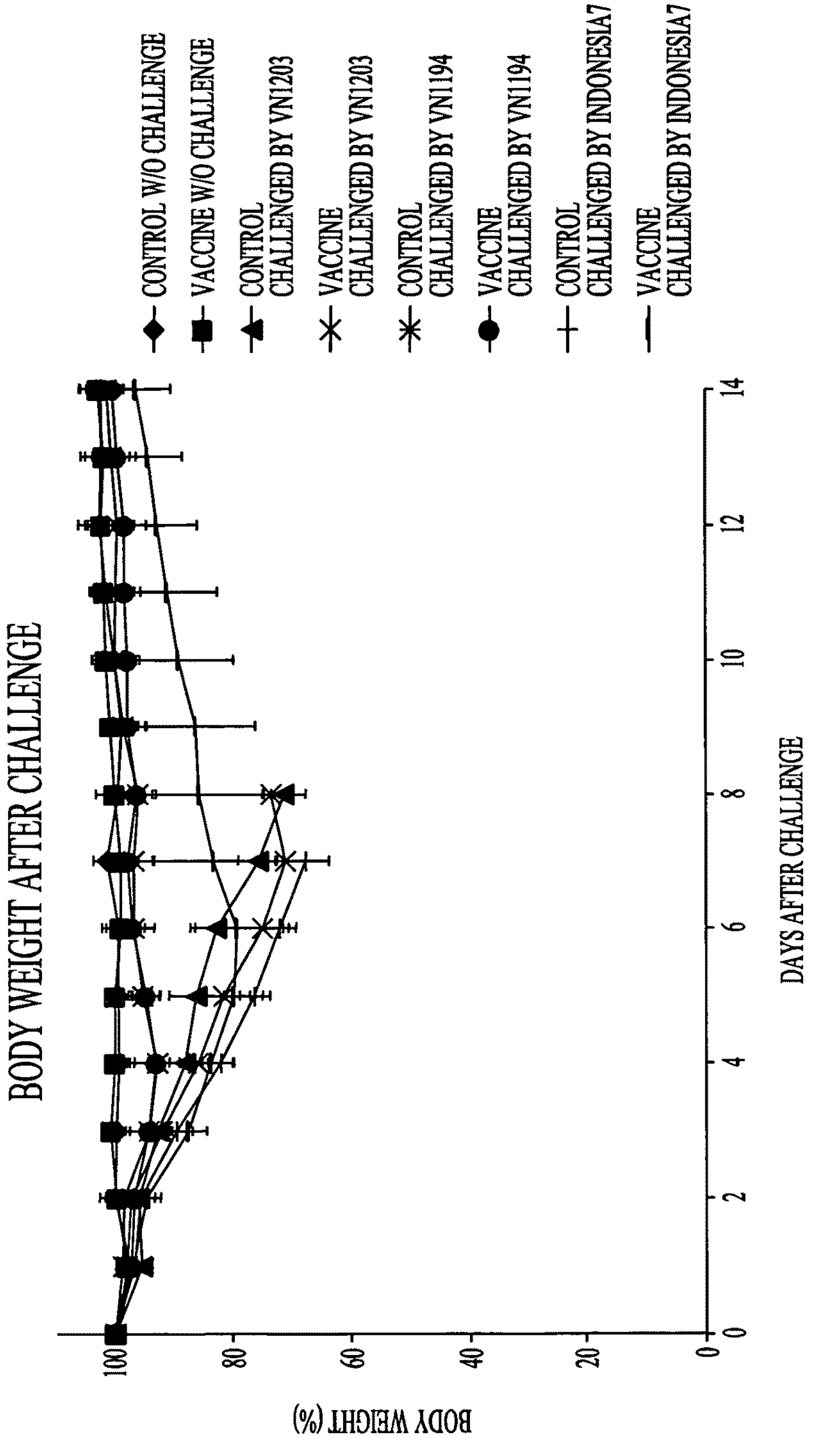
FIG. 7. Body weight after challenge. When all 8 mice in a group were not alive, the mean and standard deviation were calculated for the remaining live mice.

FIG. 4 shows the survival rates for each group of mice. All of the mice vaccinated with VN1194NA− survived a lethal challenge (100 $LD_{50}$) with highly pathogenic H5N1 viruses [wild type VN1194, A/Vietnam/1203/04 (Clade 1; VN1203), and A/Indonesia/7/05 (Clade 2; Indonesia7)], whereas all of the control mice died or had to be euthanized due to their disease by day 8 post-challenge. FIG. 6 shows antibody titers in those mice. High titers of IgG and IgA antibodies against wild-type VN1194 were detected in the serum, lung and nasal washes of vaccinated mice 14 days after immunization. Although the body weight of the vaccinated mice challenged with VN1194 and VN1203 virus dropped slightly on day 4 post-challenge, the mice recovered (FIG. 7). Similarly, the body weight of vaccinated mice challenged with Indonesia7 dropped until day 6 post-challenge; however, all of the mice again recovered completely. By contrast, the control mice did not recover. Viruses were isolated from a variety of organs in control mice, whereas virus replication was restricted to respiratory organs in vaccinated mice (FIGS. 8-9).

Summary

An A/Vietnam/1194/04(H5N1) (VN1194) mutant virus was generated that entirely lacks an NA gene (VN1194NA−), that is, it contains only seven RNA segments. In MDCK cells, this virus grew to about $10^2$ plaque-forming units (pfu) per ml of cell culture supernatant. However, after 10 consecutive passages in MDCK cells, virus titers increased to about $10^6$ pfu per ml of cell culture supernatant, suggesting that VN1194NA− had acquired mutations that allowed its efficient growth in cell culture. Nevertheless, this variant remained highly attenuated in mice, with an $MLD_{50}$ (the amount of viruses required to kill 50% of infected animals) of $>10^5$ pfu. By contrast, the $MLD_{50}$ for the parental VN1194 virus was 3.1 pfu. Hence, the 7 segment virus grows to reasonable titers in cell culture but is highly attenuated in mice, suggesting its potential for use as a live attenuated vaccine.

Example II

7 Segment Influenza Viruses and Additional Attenuating Mutations

To establish NA-deficient influenza viruses as live, attenuated vaccines, recombinant viruses of the NA-deficient influenza virus H3 and H5 subtypes are generated and evaluated. Live, attenuated, NA-deficient H3 vaccine viruses may provide protection against 'seasonal influenza'. By contrast, live, attenuated, NA-deficient H5 vaccine viruses likely are reserved for a pandemic caused by a virus of this subtype, since the use of this vaccine may introduce a new HA subtype into human populations. In the event of an H5N1 influenza virus pandemic, when viruses of this subtype are already circulating in humans, a live, attenuated H5N1 vaccine would be invaluable, as its immunogenicity would be expected to be superior to that of inactivated vaccines.

Generation of a Live, Attenuated, NA-Deficient H5N1 Virus

Highly pathogenic H5N1 influenza viruses now fall into two clades, prompting the generation of candidate vaccine viruses for each clade: NA-deficient A/Vietnam/1194/04 (VN1194, clade 1) and A/Indonesia/5/05 (Ind/05, clade 2).

To generate a NA-deficient VN1194 virus for use as a vaccine, a RNA polymerase I based plasmid for the expression of a modified HA protein encoding an avirulent-type HA cleavage site sequence is prepared. The HA protein of VN1194 HA contains a multibasic cleavage site as shown in Table 3 (cleavage occurs between the Arg and Gly residues as depicted by the arrow).

TABLE 3

| | | | | | | | | | |
|---|---|---|---|---|---|---|---|---|---|
| | | | | | | | | ↓ | |
| VN1194 | R | E | R | R | R | K | K | R | G (SEQ ID NO: 1) |
| | AGA | GAG | AGA | AGA | AGA | AAA | AAA | AGA | GGA (SEQ ID NO: 2) |
| VN1194-$HA_{Av}$ | | | | | R | E | T | R | G (SEQ ID NO: 3) |
| | | | | | AGA | GAA | ACG | AGA | GGA (SEQ ID NO: 4) |

To generate an avirulent-type HA cleavage sequence, the multibasic sequence is altered to RETR (SEQ ID NO:5), an avirulent-type sequence. The conversion of the HA cleavage site from a 'virulent' to an 'avirulent' type further attenuates the 7 segment vaccine virus. Other attenuating mutations useful for vaccine viruses such as H5 and H3 viruses are disclosed in Example III.

To generate an NA-deficient Ind/05 virus, vRNA is isolated, reverse transcribed, cloned, and sequenced. To establish a consensus sequence for this virus, at least three clones per gene segment are sequenced. Full-length viral cDNAs that adhere to the consensus sequence are cloned between RNA polymerase I promoter and terminator sequences as described in Hatta et al. (2001) and Neumann et al. (1999). A RNA polymerase I plasmid expressing a 'detoxified' HA protein of Ind/05 is also prepared.

Vero cells that are qualified for human vaccine virus production are used to generate virus. Vero cells suitable for this purpose can be obtained from ATCC. Specifically, Vero cells are transfected with 7 RNA polymerase I plasmids for the synthesis of VN1194 or Ind/05 vRNAs (encoding wild-type PB2, PB1, PA, NP, M, and NS segments, and the modified HA segment; no NA segment plasmid is included), and with 4 plasmids for the expression of the nucleoprotein and the three polymerase proteins. When a cytopathic effect (CPE) is observed, virus-containing cell culture supernatants are harvested and all 7 vRNA segments are sequenced to confirm the authenticity of the viruses (VN1194$HA_{Av}$NA− or Ind/05$HA_{Av}$NA−, respectively). Since the initial titers of VN1194$HA_{Av}$NA− and Ind/05$HA_{Av}$NA− may be low, a CPE may not initially be observed in plasmid-transfected cells. In this event, cell culture supernatant from plasmid-transfected Vero cells is collected at 96 hours post-infection and passaged once in fresh Vero cells. Once a CPE is observed, the supernatants are collected and the authenticity of the viruses tested. For the original VN1194$HA_{Av}$NA− and Ind/05$HA_{Av}$NA− virus stocks, their titers are determined by plaque assays in MDCK cells.

To obtain variants that grow to reasonable titers in cell culture, the virus is serially passaged, in parallel, in both Vero and MDCK cells. Briefly, cells are infected at a multiplicity of infection (m.o.i.) of 0.01 and virus-containing cell culture supernatants harvested when most of the cells have lysed due to virus infection. After each passage, virus titers are determined in MDCK cells. Viruses are passaged until titers reach at least $10^6$ pfu per ml of cell culture supernatant, e.g., about 8 to 12 serial passages. The variant (i.e., Vero or MDCK grown virus) that grows to the highest titers is used.

Once VN1194$HA_{Av}$NA− and Ind/05$HA_{Av}$NA− variants that grow to high titers in cell culture are obtained, stock viruses are generated, aliquoted, and stored at −80° C. Stock viruses are sequenced entirely to confirm their authenticity and to identify the mutations that arose from adaptation to Vero or MDCK cells.

In parallel, both wild-type viruses (i.e., VN1194 and Ind/05) are generated in Vero cells. These viruses are used in both live and formalin-inactivated forms as controls. For formalin-inactivated vaccines, the HA concentration is established as described in Katz et al. (1989).

Generation of an NA-Deficient H3 Virus

Following the strategy outlined above for the generation of NA-deficient H5 viruses, a NA-deficient H3 virus is generated for use against 'seasonal influenza'. Specifically, a NA-deficient virus based on the A/Yokohama/2017/03 (Yok) virus, a recent human H3N2 virus, is prepared using reverse genetics. A Yok virus that lacks the NA segment (YokNA−) is generated and high-growth variants are prepared in Vero and MDCK cells. The high-growth YokNA− variant may be developed into a master seed virus. High-growth YokNA− variants developed in Vero and MDCK cells are sequenced completely, and all mutations found in the high-growth, Vero cell grown YokNA− variant are introduced into RNA polymerase I plasmids for YokNA− generation, using site-directed mutagenesis. All mutations found in the high-growth, MDCK cell grown YokNA− variant are introduced into another set of RNA polymerase I plasmids for YokNA− generation, using site-directed mutagenesis.

As described above for H5N1 viruses, the wild-type Yok virus is also generated in Vero cells. Both live and formalin-inactivated Yok viruses serve as controls. For formalin-inactivated vaccines, the HA concentration is established.

If high-growth variants are not obtained after 15 serial passages, cell lines that produce reduced amounts of sialic acids (hence alleviating the need for NA activity) are used to support the growth of viruses that lack NA, e.g., a MDCK cell line that expresses low amounts of sialic acid (Hughes et al., 2001) and supports efficient growth of an NA-deficient virus (Shinya et al., 2004). A similar strategy may be used to establish a Vero cell line that expresses low amounts of sialic acid.

Pathogenicity and Immunogenicity of NA-Deficient H5 and H3 Influenza Viruses

Live, attenuated vaccines are sufficiently attenuated (cause no or mild disease symptoms), immunogenic (stimulate strong humoral and cellular immune responses), and protective (provide protective immunity to immunized individuals).

The following viruses are assessed for pathogenicity and immunogenicity:

TABLE 4

| H5N1 viruses | |
|---|---|
| VN1194$HA_{Av}$NA- | Live, attenuated, NA-deficient virus; avirulent HA cleavage sequence |
| VN1194 | Parental virus, live |
| $VN1194_{Inact.}$ | Parental virus, formalin-inactivated |
| Ind/05$HA_{Av}$NA- | Live, attenuated, NA-deficient virus; avirulent HA cleavage sequence |

TABLE 4-continued

| | |
|---|---|
| Ind/05 | Parental virus, live |
| Ind/$05_{Inact.}$ | Parental virus, formalin-inactivated |
| H3N2 virus | |
| YokNA- | Live, attenuated, NA-deficient virus |
| Yok | Parental virus, live |
| $Yok_{Inact.}$ | Parental virus, formalin-inactivated |

Pathogenicity and Virulence of NA-Deficient H5 viruses (VN1194$HA_{Av}$NA−, Ind/05$HA_{Av}$NA−)

Highly pathogenic H5N1 influenza viruses, such as VN1194 and Ind/05, typically kill mice within 8 days of infection. To assess the level of attenuation for VN1194$HA_{Av}$NA− and Ind/05$HA_{Av}$NA−, their $LD_{50}$ values are determined. $LD_{50}$ values are also determined for the parental VN1194 and Ind/05 viruses, but not for formalin-inactivated viruses.

Briefly, BALB/c mice (5 animals/group) and/or ferrets (3 animals/group) are inoculated intranasally with ten-fold dilutions of live, attenuated (VN1194$HA_{Av}$NA− and Ind/05$HA_{Av}$NA−) or live parental virus (starting from $10^5$ pfu) and observed daily for signs of disease. Control animals are inoculated with the same amount of live parental virus. Additional controls are mock-infected. Since highly pathogenic H5N1 influenza viruses are known to cause systemic infection, viral titers are determined in lungs, nasal turbinates, heart, spleen, kidney, liver, colon, pancreas, and brain on days 3 and 6 post-infection. VN1194$HA_{Av}$NA− and Ind/05$HA_{Av}$NA− virus, by contrast, show significant attenuation, that is, no virus spread beyond the respiratory organs and lower overall virus titers.

Pathogenicity and Virulence of an NA-Deficient H3 Virus (YokNA−)

In contrast to highly pathogenic H5N1 influenza viruses, human H3N2 viruses typically do not cause systemic infection in mice or ferrets and do not kill these animals. To establish the level of attenuation for YokNA− as compared to the parental Yok virus, mice and ferrets are infected intranasally as described above. Animals are observed daily for signs of disease such as weight loss, reduced activity, or sneezing (for ferrets). In parallel, virus titers are determined in nasal turbinates and lungs of infected animals on days 1, 3, and 6 post-infection. For Yok virus, signs of mild disease occur early in the infection, which may clear by day 6 post-infection. For YokNA− virus, low virus titers are observed on day 1 (reflecting the virus's limited ability to replicate) and less pronounced, if not no disease symptoms and little if any virus replication, are observed on day 3 post-infection Immunogenicity of NA-Deficient H5 and H3 Influenza Viruses For live, attenuated vaccines, the balance between attenuation and immunogenicity is important. To assess the immunogenicity of VN1194$HA_{Av}$NA−, Ind/05$HA_{Av}$NA−, and YokNA−, humoral and cellular immune responses are tested in mice, and a humoral response is tested in ferrets.

Hemagglutination Inhibition (HI) and Neutralization Tests.

To determine the levels of serum antibodies to HA, hemagglutination inhibition and neutralization tests are performed. Mice and ferrets are infected with ten-fold dilutions (starting with $10^5$ pfu) of VN1194$HA_{Av}$NA−, Ind/05$HA_{Av}$NA−, or YokNA virus. In parallel, control animals are infected with the same amounts of live parental virus or with 30 μg of HA for inactivated parental viruses. Mock-infected animals serve as negative controls. On days 7, 14, 30, and 90 post-infection, serum samples are collected from the suborbital capillary vein of mice (or the jugular vein of ferrets; the latter will be anesthetized for this procedure). Mice infected with live VN1194 or Ind/05 virus die within 7-8 days post-infection.

For live, attenuated and inactivated viruses, a two-dose regimen is also tested. Animals are infected as described above and then boosted with the same dose of virus 30 days later. This two-dose regimen is not conducted for live parental viruses, since mice infected with high doses die within 7-8 days of the first immunization, whereas those infected with low doses survive and develop sterile immunity (Katz et al., 2000).

For HI assays, serum samples are treated with receptor-destroying enzyme and sodium periodate, and then tested with H5 and H3 viruses. For H5 viruses, representative strains isolated since 1997 from birds and humans that cover both clades are included. For H3 viruses, representative human isolates from 2000 forward are included. HI assays are typically performed with chicken or turkey erythrocytes; however, these erythrocytes have low sensitivity for antibodies to H5 HA. Horse erythrocytes have improved sensitivity (Stephenson et al., 2004), therefore, horse erythrocytes are employed for HI assays with H5 viruses. Moreover, some human H3 viruses do not agglutinate chicken erythrocytes efficiently, but bind to guinea pig erythrocytes (Stephensen et al., 2003). For H3 viruses, HI assays are performed with guinea pig erythrocytes. The HI titer of serum is expressed as the reciprocal of the highest dilution of serum that causes the complete inhibition of 4 hemagglutination units of antigen. A fourfold increase in HI titers is considered significant; titers of 1:40 or more are believed to be protective (Porter et al., 1979).

For neutralization assays, serum samples are treated as described for HI assays, then mixed with equal volumes of homologous or heterologous virus (100 pfu each), incubated for 1 hour at room temperature, and then inoculated onto MDCK cells, following established protocols (Bridges et al., 2002). MDCK cells are infected with 100 pfu of virus in the presence of a control serum that does not react with H5N1 or H3N2 viruses. The neutralizing antibody titer is the reciprocal of the highest dilution of serum that reduces the plaque number by 50%.

Inactivated influenza vaccines produce higher serum HI titers than live, attenuated vaccine viruses (Cox et al., 2004). Thus, the serum HI titers induced by VN1194$HA_{Av}$NA−, Ind/05$HA_{Av}$NA−, and YokNA− may be low. It is possible that an antibody response is not detected in animals infected with NA-deficient viruses. While detectable serum antibody titers provide an indication of immunogenicity for inactivated vaccines, the lack of such titers does not necessarily exclude protective efficacy for the vaccine.

Antibody Response.

To further assess the humoral response to infection with VN1194$HA_{Av}$NA−, Ind/05$HA_{Av}$NA−, or YokNA− virus, IgA- and IgG-specific ELISAs are conducted on serum and bronchioalveolar lavage (BAL) samples from infected mice and ferrets.

Serum samples are obtained as described above. To obtain BAL fluid, animals are euthanized, catheterized, the tracheae and lungs washed with phosphate-buffered saline (PBS), and the fluid drawn into a syringe attached to the catheter. The levels of IgA and IgG antibodies are determined by use of established protocols (Kida et al., 1982). Briefly, the viruses used for immunization are absorbed to microtiter plates, incubated with serially diluted serum or BAL samples, washed, and incubated with anti-mouse peroxidase-conjugated IgA or IgG antibodies. Samples are then incubated with a peroxidase substrate. The reaction product is quantified on an ELISA reader at 405 nm. Samples derived from mock-infected animals are used to establish a baseline.

Inactivated influenza virus vaccines induce appreciably higher levels of serum antibodies than do live, attenuated vaccines (Cox et al., 2004). Yet, live, attenuated influenza virus vaccines are more potent inducers of IgA in nasal washes, while inactivated vaccines induce predominantly IgG mucosal antibodies. For animals infected with the live, attenuated, NA-deficient viruses and the live parental viruses, relatively low levels of serum antibodies are expected relative to animals infected with inactivated viruses. The live viruses, however, are expected to be superior to inactivated viruses with respect to inducing mucosal IgA antibodies.

Cellular Immune Response.

To assess the cellular immune responses to infection with live, attenuated NA-deficient H5 or H3 viruses, virus-specific CD8 T cell responses in mice are measured. Animals are inoculated with live parental virus, live, attenuated virus, or inactivated virus, as described above. On days 7, 14, 30, and 90 post-infection (for the parental H5 viruses, only the first time-point can be tested since animals die by day 7 or 8 post-infection), BAL fluids are collected as described above, as well as lungs, spleen and cervical and mediastinal lymph nodes. For lymph nodes and spleen, single cell suspensions of mononuclear cells are prepared as described in Hogan et al. (2001). For lungs, a cell suspension is generated according to established protocols (Masopust et al., 2001) and mononuclear cells obtained using a Percoll gradient. All mononuclear cells are then stained with labeled-MHC I tetramers specific to the influenza epitopes ($K^d$ $NP_{147-155}$:TYQRTRALV, SEQ ID NO:6; $K^d$ $HA_{518-526}$: IYSTVASSL, SEQ ID NO:7) in BALB/c mice, and with anti-CD8, anti-LFA-1, and anti-CD62L antibodies. The number of virus-specific CD8 T cells is determined by flow cytometry.

In parallel, intracellular cytokine staining is used to measure functional cytotoxic T cells. Mononuclear cells are stimulated with epitope peptides in the presence of Brefeldin A, which inhibits cytokine secretion. Staining for cell surface CD8 and intracellular IFN-γ, TNF-α, or IL-2 is achieved with a Cytofix/Cytoperm kit (BD-Pharmingen), and the number of cytokine-producing CD8 T cells is measured by flow cytometry.

Live, attenuated influenza viruses typically elicit a stronger cellular immune response than inactivated viruses. More potent virus-specific CD8 T cell stimulation is expected in animals infected with live parental viruses or live, attenuated viruses than in animals infected with inactivated viruses.

Protective Efficacy of NA-Deficient H5N1 Viruses

To assess the protective efficacy of NA-deficient viruses, groups of mice (or ferrets; 9 animals/group) are immunized intranasally with the same doses of live, attenuated, NA-deficient viruses or inactivated viruses that were tested for immunogenicity. If the immunogenicity studies show the two-dose regimen with a booster immunization to be more efficient than a single immunization, a booster immunization is also conducted for protection studies. If both regimens are of comparable efficacy, mice are immunized only once. Mock-infected animals serve as controls. One to three months post-immunization, animals are challenged with lethal doses (10 or 100 $MLD_{50}$ for mice; $10^6$ pfu for ferrets) of homologous VN1194 or Ind/05 virus. Animals are observed daily for signs of disease. On days 3 and 6 post-challenge, three animals per group are euthanized. Virus titers in organs and serum antibody titers are determined.

For mouse experiments, mock-vaccinated animals are expected to succumb to systemic infection caused by VN1194 or Ind/05 virus. For ferret experiments, mock-vaccinated animals challenged with Ind/05 virus are expected to die, whereas those infected with VN1194 are expected to lose weight but to recover from virus infection. By contrast, all vaccinated animals are expected to be protected against lethal challenge or weight loss. The live, attenuated NA-deficient viruses are expected to provide better protection than the inactivated viruses. Better protection may include higher survival rates, lower virus titers, restricted virus spread, and/or, reduced weight loss after challenge.

Vaccines to highly pathogenic H5N1 influenza viruses may provide protection against isolates from both clades. To assess whether the live, attenuated NA-deficient H5N1 vaccine viruses provide cross protection, animals are immunized as above and challenged with 10 or 100 $MLD_{50}$ (for mice), or with $10^6$ pfu (for ferrets), of the respective heterologous virus (i.e., animals immunized with VN1194$HA_{Av}$NA− (clade 1) virus are challenged with Ind/05 (clade 2) virus and vice versa). Some cross-protection is expected, although the protective efficacy may be lower than that observed with homologous virus.

Protective Efficacy of an NA-Deficient H3N2 Virus

To establish the protective efficacy of an NA-deficient H3N2 virus, immunization and challenge studies are carried out essentially as described above for H5N1 viruses. Groups of mice (and ferrets; 9 animals/group) are immunized intranasally with the same doses of YokNA− or $Yok_{Inact.}$ that are tested for immunogenicity. Mock-infected animals serve as controls. One to three months post-immunization, animals are challenged with $10^6$ pfu of Yok virus. Animals are observed daily for signs of disease. On days 3 and 6 post-challenge, three animals per group are euthanized. Virus titers in nasal turbinates and lungs and serum antibody titers are determined.

Signs of disease are expected in mock-immunized control animals but not in vaccinated animals. Limited virus replication is expected in the nasal turbinates and lungs of vaccinated animals.

If VN1194$HA_{Av}$NA−, Ind/05$HA_{Av}$NA−, and/or YokNA− are too pathogenic, additional attenuating mutations are introduced into their genomes. If the NA-deficient viruses are too attenuated, viruses that contain all 8 vRNAs but lack functional NA, for example, by deleting large portions of the NA reading frame are generated.

Example III

Live, Attenuated Equine Influenza Vaccines

Equine influenza viruses are the leading cause of respiratory diseases in horses. Only two subtypes of influenza A viruses have caused respiratory disease in horses: the H7N7 subtype (also referred to as equi-1) that has not been isolated from horses since 1989 but may still circulate in a subclinical form, and the H3N8 subtype (equi-2) which circulates throughout the world. In the late 1980's, equine H3N8 viruses diverged into two lineages (i.e., 'American' and 'Eurasian'). Current guidelines recommend that vaccines should contain a representative strain of each of the two lineages.

Current equine influenza vaccines can be divided into inactivated and live vaccines. Inactivated vaccines, i.e., inactivated whole vaccines or subunit vaccines, provide only a short-lived antibody response. Live vaccines contain replicating virus and therefore trigger both human and cellular immune responses, making them superior to inactivated vaccines. A live, attenuated influenza vaccine is now on the market that was generated by gradual cold-adaptation of A/equine/Kentucky/1/91 virus. This vaccine is safe and provides protection against homologous and heterologous viruses for several months; it, however, does not provide sterile immunity.

Reverse genetics can be used to introduce attenuating mutations into influenza viral genomes at will (Neumann et al., 1999). Reverse genetics is superior to cold-adaptation in that the level of attenuation can be adjusted by testing various mutations in various viral genes in various combinations.

To identify equine influenza viruses that grow to high titers in MDCK cells, while being attenuated in mice, a wild-type equine influenza virus is generated from plasmids. The artificially generated equine influenza virus serves as a 'parent strain' for the introduction of attenuating mutations. To develop a live, attenuated equine influenza vaccine, the vaccine may be based on a recently circulating strain to ensure antigenic similarity with viruses against which protection should be achieved. Secondly, the vaccine virus should grow to high titers in cell culture to ensure cost-efficient vaccine production. Thirdly, the non-attenuated wild-type strain should produce clinical symptoms in horses, so that the attenuation levels of the candidate vaccine viruses can be determined. A/equine/Ohio/1/2003 (H3N8; belonging to the 'American' lineage) virus that fulfills these requirements.

The artificial generation of A/eq/Ohio/1/2003 ('Eq/Ohio') virus is carried out as described in Neumann et al. (1999) and Hatta et al. (2001). Briefly, all eight viral RNA segments are reverse transcribed, PCR-amplified, and cloned. A consensus sequence is established by sequencing at least three clones per RT-PCR product. cDNA clones encoding full length RNA segments that adhere to the consensus sequence are cloned between RNA polymerase I promoter and terminator sequences. Next, 293T (human embryonic kidney) cells are transfected with the eight resulting RNA polymerase I plasmids for the transcription of viral RNAs and with four plasmids encoding the viral polymerase and NP proteins, resulting in the generation of Eq/Ohio virus. Virus is harvested from the supernatant of transfected cells and re-sequenced to confirm its authenticity. The artificially generated Eq/Ohio virus is amplified in MDCK cells and viral stocks frozen at −80° C.

To generate a live, attenuated Eq/Ohio virus, mutations that attenuate human and/or avian influenza virus strains are introduced to Eq/Ohio. Mutations may be introduced into multiple genes, which makes a reversion to wild-type phenotype less likely. Moreover, the mix-and-match of different mutant viral genes allows fine-tuning of the attenuation level.

One mutation may be at amino acid at position 627 of the PB2 protein (a component of the viral polymerase complex), which is a determinant of the pathogenicity of H5N1 influenza viruses in mammals (Hatta et al., 2001). Human influenza virus isolates contain Lys at position 627, while avian strains are characterized by Glu at that position. Several avian H5N1 viruses isolated from infected humans or other mammals contained Lys at PB2-627, suggesting strong selective pressure for this amino acid in mammalian species. Studies indicated that Lys at position 627 of the PB2 protein confers a replicative advantage in mammalian cells (Shinya et al., 2004; Massin et al., 2001). Equine influenza viruses contain Glu, i.e., the avian-like amino acid, at position 627 of their PB2 protein, and the replacement of this amino acid with other amino acids may attenuate equine influenza virus replication in horses. However, other amino acids at this position, including lysine, glycine, a small hydrophobic amino acid, tryptophan, a large hydrophobic amino acid, or proline, a so-called 'helix' breaker that typically alters the protein structure, may likewise result in attenuation.

The PB1 segment encodes the PB1 protein that is a component of the viral polymerase complex. A second protein, termed PB1-F2, is encoded in the +1 reading frame (Chen et al., 2001). In human and avian virus isolates, PB1-F2 is an 87-to-90 amino acid protein, whereas the PB1-F2 reading frame of most swine virus isolates is interrupted by stop codons. PB1-F2 induces apoptosis (Chen et al., 2001; Zamarin et al., 2005). The conservation of this reading frame among influenza A viruses suggests a role for that protein in viral replication or pathogenesis. The limited sequence data available for equine influenza viruses show that most isolates, including Eq/Ohio, contain a stop codon in their PB1-F2 reading frame that limits the length of this protein to 81 amino acids. Thus, Eq/Ohio viruses which express a full-length PB1-F2 protein of 90 amino acids, or which do not express PB1-F2 due to the introduction of stop codons downstream of the PB1-F2 start codon, are tested for viability and virulence.

The third component of the influenza viral polymerase complex, the PA protein, has been reported to have protease activity (Sanz-Ezquerro et al., 1995). This catalytic activity requires a serine residue at position 624 (Hara et al., 2001) and/or a threonine residue at position 157 (Perali et al., 2000; Sanz-Ezquerro et al., 1996). Replacement of Thr-157 with alanine resulted in mild attenuation in MDCK cells but significant attenuation in mice (Huarte et al., 2003). Hence, the virus in which Thr-157 of the Eq/Ohio PA protein is replaced with alanine may be attenuated.

The M2 protein serves as an ion channel that executes functions early and late in the viral live cycle. A human influenza virus containing a deletion in the M2 ion channel domain replicated efficiently in cell culture but was attenuated in mice (Watanabe et al., 2001). Moreover, the attenuated virus protected mice against challenge with a lethal dose of wild-type influenza virus (Watanabe et al., 2002). A similar deletion in the M2 protein of Eq/Ohio virus may similarly yield an attenuated equine influenza virus.

The NS2 protein executes a critical role in the nuclear export of viral ribonucleoprotein complexes and is therefore now also referred to as nuclear export protein, NEP. Several amino acid replacements in NEP that did not attenuated the virus in MDCK cells, resulted in viruses that were attenuated in mice.

To establish the growth kinetics of mutant Eq/Ohio viruses in MDCK cells, those cells are infected with a multiplicity of infection (m.o.i.) of 0.01 and virus titers in the cell culture supernatant are determined at 12 hours, 24 hours, 36 hours, 48 hours, and 72 hours post-infection. Artificially generated wild-type Eq/Ohio virus serves as a positive control. Mutant viruses that grow efficiently in MDCK cells, hence allowing efficient vaccine virus production, and are attenuated by no more than one log unit (as compared to wild-type Eq/Ohio viruses), are further characterized.

Viral growth kinetics in mice are determined as described in Hatta et al. (2001), to identify mutant viruses that are attenuated in mice, since these viruses may also be attenuated in horses. All mutant Eq/Ohio viruses that are attenuated by at least one log unit (as compared to wild-type Eq/Ohio virus) are further characterized.

Example IV

An H5 influenza virus vaccine that contains the HA and NA genes of a highly pathogenic H5N1 influenza virus (A/Hong Kong/213/2003) in a background of either the PR8 virus (e.g., see U.S. application Ser. No. 11/444,145, the disclosure of which is incorporated by reference herein), or an avirulent avian virus [A/whistling swan/Shimane/499/83(H5N3)], was generated. For each vaccine candidate, several variants, in which the multibasic HA cleavage site was replaced with different 'avirulent-type' sequences to 'detoxify' the vaccine virus, were prepared. All vaccine candidates grew well in eggs. When tested for their virulence in chickens, one vaccine candidate caused neurological symptoms and further analysis revealed a mutation at the HA cleavage site that generated a basic amino acid. Thus, 'detoxified' viruses may need at least two nucleotide replacements to acquire an HA multibasic cleavage site. For two variants that fulfilled this criterion, formalin-inactivated viruses were prepared and found to protect chickens against infection with lethal doses of wild-type virus.

To better understand the immune responses to highly pathogenic H5N1 viruses, tetramer assays and intracellular cytokine assays are conducted. Briefly, intracellular cytokine staining is used to examine the number of IFN-γ-producing $CD8^+$ T cells in the BAL fluid of BALB/c mice 7 days after they are infected with an H5N1 virus. For two different H5N1 viruses, IFN-γ-producing $CD8^+$ T cells were found following exposure to the $NP_{147-155}$ epitope (TYQRTRALV; SEQ ID NO:6). The $H\text{-}2K^d$ tetramer for the $NP_{147-155}$ epitope is also used to detect memory $CD8^+$ T cells in the deep cervical lymph nodes of mice several months after they were infected with an H5N1 virus.

REFERENCES

*Avery's Drug Treatment,* 1987.

Avery's, Drug Treatment: Principles and Practice of Clinical Pharmacology and Therapeutics, ADIS Press, Ltd., 3rd ed., Williams and Wilkins, Baltimore, Md. (1987).

Bachmeyer, 1975.

Berkow et al., The Merck Manual, 15th ed., Merck & Co., Rahway, N.J. 1987.

Beyer et al., *Vaccine,* 20:1340 (2002).

Bosch et al., *Virology,* 95:197 (1979).

Bresson et al., *Lancet,* 367:1657 (2006).

Bridges et al., *J. Infect. Dis.,* 185:1005 (2002).

Chen et al., *Nat. Med.,* 7:1306 (2001).

Chen et al., *Virology,* 345:416 (2006).

Couch, *Dev. Biol.* (*Basel*), 115:25 (2003).

Cox et al., eds. Topley & Wilson's Microbiology and Microbial Infections. London: Arnold, 2005:634-698.

Cox et al., *Scand. J. Immunol.,* 59:1 (2004).

Ebadi, Pharmacology, Little, Brown & Co., Boston, Mass. (1985).

Edwards, *J. Infect. Dis.,* 169:68 (1994).

Garten et al., *Trends Microbiol.,* 7:99 (1999).

Gross et al., *Ann. Intern. Med.,* 123:518 (1995).

Hara et al., *Genes Cells,* 6:87 (2001).

Hatta et al., *Philos. Trans. R. Soc. Lond. B. Biol. Sci.,* 356: 1841 (2001).

Hatta et al., *Science,* 293:1840 (2001).

Hoffmann et al., *J. Virol.,* 79:11014 (2005).

Hogan et al., *J. Immunol.,* 166:1813 (2001).

Horimoto et al., *J. Virol.,* 68:3120 (1994).

Horimoto et al., *Vaccine,* 24:3669 (2006).

Horimoto et al., *Virus Res.,* 50:35 (1997).

http://www.oie.int/downld/AVIAN%20INFLUENZA/Graph%20HPAI/graphs%20HPAI%2002__08__2006.pdf.2006.

Huarte et al., *J. Virol.,* 77:6007 (2003).

Hughes et al., *J. Virol.* 74:5206 (2000).

Hughes et al., *J. Virol.,* 75:3766 (2001).

Jin et al., *J. Virol.,* 78:995 (2004).

Jin et al., *Virology,* 306:18 (2003).

Katz et al., *Biomed. Pharmacother.,* 54:178 (2000).

Katz et al., *J. Infect. Dis.,* 160:191 (1989).

Kawaoka et al., *Virology,* 139:303 (1984).

Kida et al., *Virology,* 122:38 (1982).

Kilbourne, *Bull. M2 World Health Org.,* 41:643 (1969).

Lamb et al., In: Knipe D M, Howley P M, Griffin D E, Martin M A, Lamb R A, Roizman B, Straus S E, eds. Fields Virology. Philadelphia: Lippincott Williams & Wilkins, 2001:1487-1532.

Lipatov et al., *J. Infect. Dis.,* 191:1216 (2005).

Liu et al., *J. Virol.,* 69:1099 (1995).

Maassab et al., *Rev. Med. Virol.,* 9:237 (1999).

Masopust et al., *Science,* 291:2413 (2001).

Massin et al., *J. Virol.* 75:5398 (2001).

Mizrahi, ed., *Viral Vaccines*, Wiley-Liss, NY (1990).

Murphy, *Inf. Dis. Clin. Practice,* 1:174 (1993).

Neumann et al., *J. Gen. Virol.,* 83:2635 (2002).

Neumann et al., *Proc. Natl. Acad. Sci. USA,* 96:9345 (1999).

Neumann et al., *Rev. Med. Virol.,* 12:13 (2002).

Nichol et al., *Arch. Intern. Med.,* 158:1769 (1998).

Ogra et al., *J. Infect. Dis.,* 135:499 (1977).

Perales et al., *J. Virol.,* 74:1307 (2000).

Potter, *Br. Med. Bull.,* 35:69 (1979).

Robertson et al., *Giornale di Igiene e Medicina Preventiva,* 29:4 (1988).

Robertson et al., *Biologicals,* 20:213 (1992).

Sanz-Ezquerro et al., *J. Virol.,* 69:2420 (1995).

Sanz-Ezquerro et al., *J. Virol.,* 70:1905 (1996).

Shinya et al., *J. Virol.,* 78:3083 (2004).

Shinya et al., *Virology,* 320:258 (2004).

Smith et al., *Cochrane Database Syst. Rev.,* 2006.

Stephenson et al., *J. Med. Virol.,* 70:391 (2003).

Stephenson et al., *Virus Res.,* 103:91 (2004).

Stieneke-Grober et al., *EMBO J.,* 11:2407 (1992).

Subbarao et al., *J. Virol.,* 67:7223 (1993).

Treanor et al., *N. Engl. J. Med.,* 354:1343 (2006).

Wagner et al., *Rev. Med. Virol.,* 12:159 (2002).

Watanabe et al., *J. Virol.,* 75:5656 (2001).

Watanabe et al., *Virology,* 299:266 (2002).

Webster et al., *Microbiol. Rev.,* 56:152 (1977).

Wiley et al., *Annu. Rev. Biochem.,* 56:365 (1987).

Zamarin et al., *PLoS Pathog.,* 1:e4 (2005).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A composition to prepare a 7 segment influenza A or B virus, comprising:

one or more vectors which include transcription cassettes for vRNA production and transcription cassettes for mRNA production, wherein the transcription cassettes for vRNA production are a transcription cassette comprising a PolI promoter operably linked to an influenza virus PA cDNA linked to a PolI transcription termination sequence, a transcription cassette comprising a PolI promoter operably linked to an influenza virus PB1 cDNA linked to a PolI transcription termination sequence, a transcription cassette comprising a PolI promoter operably linked to an influenza virus PB2 cDNA linked to a PolI transcription termination sequence, a transcription cassette comprising a PolI promoter operably linked to an influenza virus HA cDNA linked to a PolI transcription termination sequence, a transcription cassette comprising a PolI promoter operably linked to an influenza virus NP cDNA linked to a PolI transcription termination sequence, a transcription cassette comprising a PolI promoter operably linked to an influenza virus M cDNA linked to a PolI transcription termination sequence, and a transcription cassette comprising a PolI promoter operably linked to an influenza virus NS cDNA linked to a PolI transcription termination sequence; and wherein the transcription cassettes for mRNA production are a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and a transcription cassette comprising a PolII promoter operably linked to a DNA coding region for influenza virus NP linked to a PolII transcription termination sequence, and wherein the composition does not include sequences corresponding to NA coding or noncoding sequences for vRNA production and sequences for mRNA production of NA.

2. The composition of claim 1, wherein each transcription cassette is on a plasmid vector.

3. The composition of claim 1, wherein one or more transcription cassettes are on one or more plasmid vectors.

4. The composition of claim 3, wherein one plasmid vector has transcription cassettes for vRNA production of PA, PB1, PB2, HA, NP, M and NS.

5. The composition of claim 3 or 4, wherein one plasmid vector has one of the transcription cassette for mRNA production and another plasmid vector has the other three transcription cassettes for mRNA production.

6. The composition of claim 3 or 4, which has four plasmid vectors for mRNA production each with one of the transcription cassettes for mRNA production.

7. The composition of claim 3, wherein one plasmid vector has six of the transcription cassettes for vRNA production and another plasmid vector has the other transcription cassette for vRNA production.

8. The composition of claim 7, wherein one plasmid vector has one of the transcription cassettes for mRNA production and another plasmid vector has the other three transcription cassettes for mRNA production.

9. The composition of claim 7, which has four plasmid vectors for mRNA production.

10. The composition of claim 3, 4 or 7, wherein one plasmid has the four transcription cassettes for mRNA production.

11. The composition of claim 1, further comprising a transcription cassette comprising a promoter linked to 5' influenza virus sequences comprising 5' influenza virus noncoding sequences linked to a DNA of interest linked to 3' influenza virus sequences comprising 3' influenza virus noncoding sequences linked to a transcription termination sequence.

12. The composition of claim 11, where the transcription cassette comprising the DNA of interest is on a plasmid vector.

13. The composition of claim 12, wherein the transcription cassette comprising the DNA of interest is on a different plasmid vector than the transcription cassettes for vRNA production.

14. The composition of claim 12, wherein the transcription cassette comprising the DNA of interest is on a different plasmid vector than one or more of the transcription cassettes for mRNA production.

15. The composition of claim 12, wherein the transcription cassette comprising the DNA of interest is on a plasmid vector having one of the transcription cassettes for vRNA production.

16. The composition of claim 12, wherein the transcription cassette comprising the DNA of interest is on a plasmid vector having one of the transcription cassettes for mRNA production.

17. A composition to prepare a 7 segment influenza A or B virus, comprising:

one or more vectors which include transcription cassettes for vRNA production, wherein the transcription cassettes for vRNA production are a transcription cassette comprising a PolI promoter operably linked to an influenza virus PA cDNA linked to a PolI transcription termination sequence, a transcription cassette comprising a PolI promoter operably linked to an influenza virus PB1 cDNA linked to a PolI transcription termination sequence, a transcription cassette comprising a PolI promoter operably linked to an influenza virus PB2 cDNA linked to a PolI transcription termination sequence, a transcription cassette comprising a PolI promoter operably linked to an influenza virus HA cDNA linked to a PolI transcription termination sequence, a transcription cassette comprising a PolI promoter operably linked to an influenza virus NP cDNA linked to a PolI transcription termination sequence, a transcription cassette comprising a PolI promoter operably linked to an influenza virus M cDNA linked to a PolI transcription termination sequence, and a transcription cassette comprising a PolI promoter operably linked to an influenza virus NS cDNA linked to a PolI transcription termination sequence, and wherein the composition does not include sequences corresponding to NA coding or noncoding sequences for vRNA production and sequences for mRNA production of NA.

18. The composition of claim 17, wherein each transcription cassette is on a plasmid vector.

19. The composition of claim 18, wherein one or more transcription cassettes are on one or more plasmid vectors.

20. The composition of claim 19, wherein one plasmid vector has transcription cassettes for vRNA production of PA, PB1, PB2, HA, NP, M and NS.

21. The composition of claim 19 or 20, wherein one plasmid vector has six of the transcription cassettes for vRNA production and another plasmid vector has the other transcription cassette for vRNA production.

22. The composition of claim 20, further comprising one plasmid vector having one transcription cassette for mRNA production and another plasmid vector having three transcription cassettes for mRNA production, wherein the transcription cassettes encode influenza virus PA, PB1, PB2 and NP.

23. The composition of claim 20, further comprising four plasmids for mRNA production, each with a different transcription cassette for mRNA production, wherein the transcription cassettes encode influenza virus PA, PB1, PB2 and NP.

24. The composition of claim 17, further comprising a transcription cassette comprising a promoter linked to 5' influenza virus sequences comprising 5' influenza virus non-coding sequences linked to a DNA of interest linked to 3' influenza virus sequences comprising 3' influenza virus non-coding sequences linked to a transcription termination sequence.

25. The composition of claim 24, wherein the transcription cassette comprising the DNA of interest is on a plasmid vector.

26. The composition of claim 25, wherein the transcription cassette comprising the DNA of interest is on a different plasmid vector than the transcription cassettes for vRNA production.

27. The composition of claim 26, wherein the transcription cassette comprising the DNA of interest is on a plasmid vector having one of the transcription cassettes for vRNA production.

28. The composition of claim 1 or 17, wherein the HA is a type A HA.

29. The composition of claim 28, wherein the HA is a H5 or H3 HA.

30. The composition of claim 1 or 17, wherein the HA is a type B HA.

31. The composition of claim 1 or 17, wherein the HA cDNA encodes an avirulent cleavage site.

32. The composition of claim 1 or 17, wherein the PB2 protein confers a cold sensitive phenotype to the prepared influenza A or B virus.

33. A method to prepare attenuated influenza A or B virus, comprising: contacting a cell with the composition of claim 1 or 17, in an amount effective to yield attenuated influenza A or B virus.

34. A method to prepare attenuated 7 segment influenza A or B virus, comprising contacting a cell with one or more vectors which include transcription cassettes for vRNA production and transcription cassettes for mRNA production, wherein the transcription cassettes for vRNA production are a transcription cassette comprising a PolI promoter operably linked to an influenza virus PA cDNA linked to a PolI transcription termination sequence, a transcription cassette comprising a PolI promoter operably linked to an influenza virus PB1 cDNA linked to a PolI transcription termination sequence, a transcription cassette comprising a PolI promoter operably linked to an influenza virus PB2 cDNA linked to a PolI transcription termination sequence, a transcription cassette comprising a PolI promoter operably linked to an influenza virus HA cDNA linked to a PolI transcription termination sequence, a transcription cassette comprising a PolI promoter operably linked to an influenza virus NP cDNA linked to a PolI transcription termination sequence, a transcription cassette comprising a PolI promoter operably linked to an influenza virus M cDNA linked to a PolI transcription termination sequence, and a transcription cassette comprising a PolI promoter operably linked to an influenza virus NS cDNA linked to a PolI transcription termination sequence; and wherein the transcription cassettes for mRNA production are a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence, and wherein the cell is not contacted with sequences corresponding to NA coding or noncoding sequences for vRNA production and sequences for mRNA production of NA so that the attenuated 7 segment influenza A or B virus produced by the cell does not have a NA gene segment and does not have NA protein.

35. A method to prepare attenuated 7 segment influenza A or B virus, comprising contacting a cell with one or more vectors which include transcription cassettes for vRNA production, wherein the transcription cassette for vRNA production are a transcription cassette comprising a PolI promoter operably linked to an influenza virus PA cDNA linked to a PolI transcription termination sequence, a transcription cassette comprising a PolI promoter operably linked to an influenza virus PB1 cDNA linked to a PolI transcription termination sequence, a transcription cassette comprising a PolI promoter operably linked to an influenza virus PB2 cDNA linked to a PolI transcription termination sequence, a transcription cassette comprising a PolI promoter operably linked to an influenza virus HA cDNA linked to a PolI transcription termination sequence, a transcription cassette comprising a PolI promoter operably linked to an influenza virus NP cDNA linked to a PolI transcription termination sequence, a transcription cassette comprising a PolI promoter operably linked to an influenza virus M cDNA linked to a PolI transcription termination sequence, and a transcription cassette comprising a PolI promoter operably linked to an influenza virus NS cDNA linked to a PolI transcription termination sequence, wherein the cell is contacted with eight transcription cassettes for vRNA, and wherein the cell is not contacted with sequences corresponding to NA coding or noncoding sequences for vRNA production and sequences for mRNA production of NA so that the attenuated 7 segment influenza virus produced by the cell does not have a NA gene segment and does not have NA protein.

36. The method of claim 34 or 35, further comprising a transcription cassette comprising a promoter linked to 5' influenza virus sequences comprising 5' influenza virus non-coding sequences linked to a DNA of interest linked to 3' influenza virus sequences comprising 3' influenza virus non-coding sequences linked to a transcription termination sequence.

37. The method of claim 34 or 35, further comprising passaging the virus in a different cell type or eggs.

38. The method of claim 34 or 35, wherein the cells that are transfected are 293T cells or Vero cells.

39. The method of claim 37, wherein the cells that are transfected are 293T cells and the virus is passaged in Vero cells.

40. The method of claim 34 or 35, further comprising isolating the virus.

41. An isolated virus prepared by the method of claim 40.

42. A vaccine comprising the isolated virus of claim 41.

43. The vaccine of claim 42, wherein the isolated virus is an influenza A virus.

44. The vaccine of claim 43, further comprising an influenza B virus.

45. The vaccine of claim 42, further comprising granulocyte macrophage-colony stimulating factor (GM-CSF).

46. A plasmid for attenuated 7 segment influenza A or B virus production comprising: a transcription cassette comprising a PolI promoter operably linked to an influenza virus PA cDNA linked to a PolI transcription termination sequence, a transcription cassette comprising a PolI promoter operably linked to an influenza virus PB1 cDNA linked to a PolI transcription termination sequence, a transcription cassette comprising a PolI promoter operably linked to an influenza virus PB2 cDNA linked to a PolI transcription termination sequence, a transcription cassette comprising a PolI promoter operably linked to an influenza virus HA cDNA linked to a PolI transcription termination sequence, a transcription cassette comprising a PolI promoter operably linked to an influenza virus NP cDNA linked to a PolI transcription termination sequence, a transcription cassette comprising a PolI promoter operably linked to an influenza virus M cDNA linked to a PolI transcription termination sequence, and a transcription cassette comprising a PolI promoter operably linked to an influenza virus NS cDNA linked to a PolI transcription termination sequence, and wherein the plasmid does not contain sequences corresponding to NA coding or noncoding sequences for vRNA production and sequences for mRNA production of NA.

47. One or more plasmids for attenuated 7 segment influenza A or B virus production comprising a transcription cassette comprising a PolI promoter operably linked to an influenza virus HA cDNA linked to a PolI transcription termination sequence, a transcription cassette comprising a PolI promoter operably linked to an influenza virus M cDNA linked to a PolI transcription termination sequence, a transcription cassette comprising a PolI promoter operably linked to an influenza virus NS cDNA linked to a PolI transcription termination sequence, a transcription cassette comprising a PolI promoter and a PolI transcription termination sequence and a PolII promoter and a PolII transcription termination sequence each operably linked to a DNA segment for influenza virus PA, a transcription cassette comprising a PolI promoter and a PolI transcription termination sequence and a PolII promoter and PolII transcription termination sequence each operably linked to a DNA segment for influenza virus PB1, a transcription cassette comprising a PolI promoter and a PolI transcription termination sequence and a PolII promoter and a PolII transcription termination sequence each operably linked to a DNA segment encoding influenza virus PB2, and a transcription cassette comprising a PolI promoter and a PolI transcription termination sequence and a PolII promoter and a PolII transcription termination sequence each operably linked to a DNA segment for influenza virus NP, and wherein the one or more plasmids do not contain sequences corresponding to NA coding or noncoding sequences for vRNA production and sequences for mRNA production of NA.

48. A method to prepare attenuated 7 segment influenza virus, comprising: contacting a cell with the plasmid of claim 46 or 47 in an effective amount.

49. An isolated population of cells comprising individual cells having transcription cassettes for vRNA production and transcription cassettes for mRNA production for attenuated 7 segment influenza A or B virus production, wherein the transcription cassettes for vRNA production are a transcription cassette comprising a PolI promoter operably linked to an influenza virus PA cDNA linked to a PolI transcription termination sequence, a transcription cassette comprising a PolI promoter operably linked to an influenza virus PB1 cDNA linked to a PolI transcription termination sequence, a transcription cassette comprising a PolI promoter operably linked to an influenza virus PB2 cDNA linked to a PolI transcription termination sequence, a transcription cassette comprising a PolI promoter operably linked to an influenza virus HA cDNA linked to a PolI transcription termination sequence, a transcription cassette comprising a PolI promoter operably linked to an influenza virus NP cDNA linked to a PolI transcription termination sequence, a transcription cassette comprising a PolI promoter operably linked to an influenza virus M cDNA linked to a PolI transcription termination sequence, and a transcription cassette comprising a PolI promoter operably linked to an influenza virus NS cDNA linked to a PolI transcription termination sequence; and wherein the transcription cassettes for mRNA production are a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and a transcription cassette comprising a PolII promoter operably linked to a DNA coding region for influenza virus NP linked to a PolII transcription termination sequence, and wherein the population of cells does not include sequences corresponding to NA coding or noncoding sequences for vRNA production and does not include sequences for mRNA production of NA.

50. The composition of claim 21, further comprising one plasmid vector having one transcription cassette for mRNA production and another plasmid vector having three transcription cassettes for mRNA production, wherein the transcription cassettes encode influenza virus PA, PB1, PB2 and NP.

51. The composition of claim 21, further comprising one plasmid vector having one transcription cassette for mRNA production and another plasmid vector having three transcription cassettes for mRNA production, wherein the transcription cassettes encode influenza virus PA, PB1, PB2 and NP.

* * * * *

UNITED STATES PATENT AND TRADEMARK OFFICE

CERTIFICATE OF CORRECTION

PATENT NO. : 8,597,661 B2
APPLICATION NO. : 12/113690
DATED : December 3, 2013
INVENTOR(S) : Kawaoka et al.

It is certified that error appears in the above-identified patent and that said Letters Patent is hereby corrected as shown below:

On the title page, in column 2, References Cited, under "Other Publications", line 11, after "11/644,179", insert --,--, therefor On title page 2, in column 1, References Cited, under "Other Publications", line 9, delete "163546," and insert --163,546,--, therefor On title page 2, in column 1, References Cited, under "Other Publications", line 10, delete "2010"." and insert --2010", 2 pgs.--, therefor On title page 2, in column 1, References Cited, under "Other Publications", line 29, delete "06-19-7-10-08", 18 pgs." and insert --Jul. 10, 2008", 15 pgs.--, therefor On title page 2, in column 1, References Cited, under "Other Publications", line 33, delete "2pgs." and insert --2 pgs.--, therefor On title page 2, in column 1, References Cited, under "Other Publications", line 46, delete "W," and insert --W.,--, therefor On title page 2, in column 1, References Cited, under "Other Publications", line 49, delete "R," and insert --R.,--, therefor On title page 2, in column 1, References Cited, under "Other Publications", line 49, delete "a" and insert --A--, therefor On title page 2, in column 1, References Cited, under "Other Publications", line 52, delete "R," and insert --R.,--, therefor On title page 2, in column 2, References Cited, under "Other Publications", line 13, delete "D," and insert --D.,--, therefor Signed and Sealed this
Twenty-seventh Day of January, 2015

Michelle K. Lee

Michelle K. Lee
*Deputy Director of the United States Patent and Trademark Office*

On title page 2, in column 2, References Cited, under “Other Publications”, line 13, delete “Misce” and insert --Mice--, therefor On title page 2, in column 2, References Cited, under “Other Publications”, line 14, delete “HINI” and insert --H1N1--, therefor On title page 2, in column 2, References Cited, under “Other Publications”, line 14, delete “H3NB” and insert --H3N8--, therefor On title page 2, in column 2, References Cited, under “Other Publications”, line 18, delete “P,” and insert --P.,--, therefor On title page 2, in column 2, References Cited, under “Other Publications”, line 23, delete “Y,” and insert --Y.,--, therefor On title page 2, in column 2, References Cited, under “Other Publications”, line 32, delete “A,” and insert --A.,--, therefor On title page 2, in column 2, References Cited, under “Other Publications”, line 35, delete “E,” and insert --E.,--, therefor On title page 2, in column 2, References Cited, under “Other Publications”, line 42, delete “T,” and insert --T.,--, therefor On title page 2, in column 2, References Cited, under “Other Publications”, line 46, delete “T,” and insert --T.,--, therefor On title page 2, in column 2, References Cited, under “Other Publications”, line 49, delete “T,” and insert --T.,--, therefor On title page 2, in column 2, References Cited, under “Other Publications”, line 58, delete “S,” and insert --S.,--, therefor On title page 3, in column 1, References Cited, under “Other Publications”, line 8, delete “M,” and insert --M.,--, therefor On title page 3, in column 1, References Cited, under “Other Publications”, line 11, delete “P,” and insert --P.,--, therefor On title page 3, in column 1, References Cited, under “Other Publications”, line 13, delete “Vaccine,23(22),” and insert --Vaccine, 23(22),--, therefor On title page 3, in column 1, References Cited, under “Other Publications”, line 14, delete “J,” and insert --J.,--, therefor On title page 3, in column 1, References Cited, under “Other Publications”, line 18, delete “R,” and insert --R.,--, therefor On title page 3, in column 1, References Cited, under “Other Publications”, line 42, delete “K,” and insert --K.,--, therefor On title page 3, in column 1, References Cited, under “Other Publications”, line 46, delete “P,” and insert --P.,--, therefor On title page 3, in column 2, References Cited, under “Other Publications”, line 12, delete “S,” and insert --S.,--, therefor On title page 3, in column 2, References Cited, under “Other Publications”, line 14, delete “αβTCR” and insert --αβ TCR$^1$--, therefor On title page 3, in column 2, References Cited, under “Other Publications”, line 22, before “mailed”, delete “Received”, therefor On title page 3, in column 2, References Cited, under “Other Publications”, line 25, delete “163546,” and insert --163,546,--, therefor On title page 3, in column 2, References Cited, under “Other Publications”, line 25, delete “Filed” and insert --filed--, therefor On title page 3, in column 2, References Cited, under “Other Publications”, line 33, delete “Filed” and insert --filed--, therefor In the Claims In column 42, line 1, in Claim 48, after “influenza”, insert --A or B--, therefor In column 42, line 56-61, in Claim 51, delete “51. The composition of claim 21, further comprising one plasmid vector having one transcription cassette for mRNA production and another plasmid vector having three transcription cassettes for mRNA production, wherein the transcription cassettes encode influenza virus PA, PB1, PB2 and NP.” and insert --51. The composition of claim 21, further comprising four plasmids for mRNA production, each with a different transcription cassette for mRNA production, wherein the transcription cassettes encode influenza virus PA, PB1, PB2 and NP.--, therefor

SEQUENCE LISTING

```
<160> NUMBER OF SEQ ID NOS: 7

<210> SEQ ID NO 1
<211> LENGTH: 9
<212> TYPE: PRT
<213> ORGANISM: Influenza Virus
```

-continued

<400> SEQUENCE: 1

```
Arg Glu Arg Arg Arg Lys Lys Arg Gly
1               5
```

<210> SEQ ID NO 2
<211> LENGTH: 27
<212> TYPE: DNA
<213> ORGANISM: Influenza Virus

<400> SEQUENCE: 2

```
agagagagaa gaagaaaaaa gagagga                                          27
```

<210> SEQ ID NO 3
<211> LENGTH: 5
<212> TYPE: PRT
<213> ORGANISM: Artificial Sequence
<220> FEATURE:
<223> OTHER INFORMATION: A synthetic altered multibasic sequence

<400> SEQUENCE: 3

```
Arg Glu Thr Arg Gly
1               5
```

<210> SEQ ID NO 4
<211> LENGTH: 15
<212> TYPE: DNA
<213> ORGANISM: Artificial Sequence
<220> FEATURE:
<223> OTHER INFORMATION: A synthetic altered multibasic sequence

<400> SEQUENCE: 4

```
agagaaacga gagga                                                       15
```

<210> SEQ ID NO 5
<211> LENGTH: 4
<212> TYPE: PRT
<213> ORGANISM: Artificial Sequence
<220> FEATURE:
<223> OTHER INFORMATION: A synthetic altered multibasic sequence

<400> SEQUENCE: 5

```
Arg Glu Thr Arg
1
```

<210> SEQ ID NO 6
<211> LENGTH: 9
<212> TYPE: PRT
<213> ORGANISM: Influenza Virus

<400> SEQUENCE: 6

```
Thr Tyr Gln Arg Thr Arg Ala Leu Val
1               5
```

<210> SEQ ID NO 7
<211> LENGTH: 9
<212> TYPE: PRT
<213> ORGANISM: Influenza Virus

<400> SEQUENCE: 7

```
Ile Tyr Ser Thr Val Ala Ser Ser Leu
1               5
```